US009763763B2

(12) United States Patent
Ostrovsky et al.

(10) Patent No.: US 9,763,763 B2
(45) Date of Patent: Sep. 19, 2017

(54) MULTI-ARM INSIDE-OUT TOOL FOR DELIVERING IMPLANTS AND METHODS THEREOF

(75) Inventors: Isaac Ostrovsky, Wellesley, MA (US); Jozef Slanda, Milford, MA (US); Brent Palmisano, Fiskdale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 442 days.

(21) Appl. No.: 13/416,488

(22) Filed: Mar. 9, 2012

(65) Prior Publication Data

US 2012/0232573 A1     Sep. 13, 2012

Related U.S. Application Data

(60) Provisional application No. 61/451,340, filed on Mar. 10, 2011.

(51) Int. Cl.
| | |
|---|---|
| *A61F 2/02* | (2006.01) |
| *A61F 2/00* | (2006.01) |
| *A61B 17/04* | (2006.01) |
| *A61B 17/062* | (2006.01) |
| *A61B 17/00* | (2006.01) |
| *A61B 17/06* | (2006.01) |
| *A61B 17/28* | (2006.01) |

(52) U.S. Cl.
CPC ........ *A61F 2/0045* (2013.01); *A61B 17/0482* (2013.01); *A61B 17/062* (2013.01); *A61B 2017/00805* (2013.01); *A61B 2017/06042* (2013.01); *A61B 2017/2837* (2013.01); *A61B 2217/005* (2013.01); *A61B 2217/007* (2013.01); *A61F 2002/0072* (2013.01)

(58) Field of Classification Search
CPC .......... A61F 2002/0072; A01K 15/003; A61B 2017/06104
USPC ............ 600/37; 606/222, 223, 146; 119/866
See application file for complete search history.

(56) References Cited

U.S. PATENT DOCUMENTS 3,946,740 A * 3/1976 Bassett .......................... 606/145
4,312,337 A * 1/1982 Donohue ............ A61B 17/1796
606/103

(Continued)

FOREIGN PATENT DOCUMENTS

| EP | 0315371 A2 | 5/1989 |
|---|---|---|
| EP | 2033583 A1 | 3/2009 |

(Continued)

OTHER PUBLICATIONS

Search Report and Written Opinion for International Application No. PCT/US2012/053105, mailed Dec. 11, 2012, 22 pages.

(Continued)

*Primary Examiner* — Charles A Marmor, II
*Assistant Examiner* — Shannon McBride
(74) *Attorney, Agent, or Firm* — Brake Hughes Bellermann LLP

(57) ABSTRACT

In a general aspect, a medical device can include an external arm having a receiving mechanism, and an internal arm coupled to the external arm such that the receiving mechanism of the external arm is movable with respect to the internal arm. The medical device can also include a sliding component including a needle configured to be coupled to a portion of an implant and configured to slidably move the needle toward the receiving mechanism of the external arm.

10 Claims, 14 Drawing Sheets

(56) References Cited

U.S. PATENT DOCUMENTS

| | | | |
|---|---|---|---|
| 4,923,461 A * | 5/1990 | Caspari et al. | 606/146 |
| 7,833,235 B2 * | 11/2010 | Chu | 606/144 |
| 9,345,472 B2 | 5/2016 | Ostrovsky | |
| 2002/0068948 A1 | 6/2002 | Stormby et al. | |
| 2003/0065337 A1 | 4/2003 | Topper et al. | |
| 2004/0106847 A1 | 6/2004 | Benderev | |
| 2004/0225305 A1 | 11/2004 | Ewers et al. | |
| 2004/0225385 A1 | 11/2004 | Takagi et al. | |
| 2006/0293554 A1 * | 12/2006 | Crawford | 600/29 |
| 2008/0188890 A1 | 8/2008 | Weitzner et al. | |
| 2009/0062819 A1 | 3/2009 | Burkhart et al. | |
| 2009/0259092 A1 * | 10/2009 | Ogdahl et al. | 600/30 |
| 2010/0137888 A1 | 6/2010 | Wulc et al. | |
| 2010/0261955 A1 | 10/2010 | O'Hern et al. | |
| 2010/0274074 A1 | 10/2010 | Khamis et al. | |
| 2010/0305581 A1 | 12/2010 | Hart | |
| 2011/0160529 A1 | 6/2011 | Crawford | |
| 2013/0060261 A1 | 3/2013 | Ostrovsky et al. | |
| 2016/0235401 A1 | 8/2016 | Ostrovsky | |

FOREIGN PATENT DOCUMENTS

| | | |
|---|---|---|
| EP | 2255733 A1 | 12/2010 |
| WO | 96/39948 A1 | 12/1996 |
| WO | 2007/106897 A2 | 9/2007 |
| WO | 2009/075800 A1 | 6/2009 |
| WO | 2012/122476 A2 | 9/2012 |
| WO | 2013/033373 A1 | 3/2013 |

OTHER PUBLICATIONS

Final Office Action for U.S. Appl. No. 13/598,143, mailed on Feb. 4, 2015, 20 pages.

Non-Final Office Action for U.S. Appl. No. 13/598,143, mailed on Jul. 1, 2015, 17 pages.

International Preliminary Report on Patentability for PCT Patent Application No. PCT/US2012/053105, issued on Mar. 4, 2014, 8 pages.

* cited by examiner

MULTI-ARM INSIDE-OUT TOOL FOR DELIVERING IMPLANTS AND METHODS THEREOF

CROSS REFERENCE TO RELATED APPLICATION

This application is a Nonprovisional of, and claims priority to, U.S. Provisional Application No. 61/451,340, filed on Mar. 10, 2011, entitled "A MULTI-ARM INSIDE-OUT TOOL FOR DELIVERING IMPANTS AND METHODS THEREOF", which is incorporated by reference herein in its entirety.

TECHNICAL FIELD

This disclosure relates generally to medical devices and more particularly to medical devices that are configured to place or deliver implants within a body of a patient.

BACKGROUND

A variety of medical procedures are performed to provide support to portions of a body of a patient. For example, some medical procedures are performed to treat various pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient using an insertion or delivery tool. The insertion tools used to deliver the implants within a body of a patient typically include a curved portion and a sharp needle or point at one end. Some of the insertion tools used to deliver the implants can be uncontrollable and can deviate from the desired direction during the implantation process. Also, some of the insertion tools used to deliver the implants have large needles that can cause undesirable levels of trauma to tissues during the implantation process. Accordingly, complications, such as inadvertent tissue, nerve, bladder, or uretheral damage can occur during the implantation process. Such complications can also occur if the shape or curvature of the insertion tool is inappropriate for delivering the implant to the desired location within the body of the patient. Thus, it would be desirable to provide an insertion tool that may be used to deliver an implant to a location within a body of a patient without damaging tissue and/or adjacent nerves or organs in an undesirable fashion.

SUMMARY

In a general aspect, a medical device can include an external arm having a receiving mechanism, and an internal arm coupled to the external arm such that the receiving mechanism of the external arm is movable with respect to the internal arm. The medical device can also include a sliding component including a needle configured to be coupled to a portion of an implant and configured to slidably move the needle toward the receiving mechanism of the external arm.

In another general aspect, a medical device can include an internal arm defining a guide, and an external arm coupled to the internal arm and having a receiving mechanism configured to move from a first position to a second position such that a distance between the guide of the internal arm and the receiving mechanism of the external arm is decreased. The medical device can also include a sliding component including a needle and configured to slidably move along the guide such that a distal portion of the needle is moved toward the receiving mechanism of the external arm.

In yet another general aspect, a method can include inserting at least a portion of an internal arm including a needle coupled to at least a portion of an implant into a body of a patient such that an external arm coupled to the internal arm is disposed outside of the body of the patient. The method can also include moving a component such that the portion of the implant coupled to the needle of the sliding component is moved along a guide of the internal arm toward the external arm and outside of the body of the patient.

DETAILED DESCRIPTION

Figure 1:
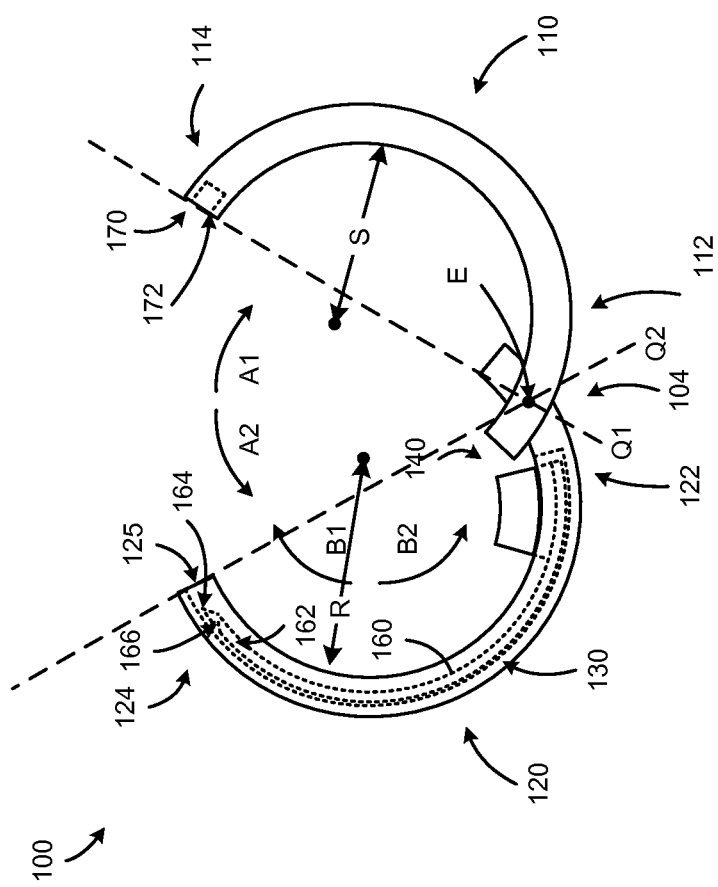
FIG. 1 is a schematic diagram of a medical device according to an embodiment.

The devices and methods described herein are generally directed to insertion or delivery tools for placing implants within a body of a patient. The implants delivered with the insertion or delivery tools may be used in any portion of a body of a patient. In some embodiments, the implants include, but are not limited to, implants that are placed within a pelvic region of a patient. For example, the implants that may be placed with the disclosed insertion or delivery tools include posterior support implants, anterior support implants, and/or total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) and/or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient and/or a male patient.

In some embodiments, the disclosed insertion or delivery tool(s) may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or a posterior vaginal incision. In some embodiments, a procedure may include an exterior incision.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted). The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that remains outside of the body of the patient or is inserted into the body after the leading end.

Various embodiments of insertion or delivery tools are described herein. The insertion or delivery tool may be used to deliver a variety of different implants into the body of a patient and only some examples of implants are described herein.

FIG. 1 is a schematic diagram of a medical device 100. The medical device 100 is configured to be used as an insertion tool or delivery tool to implant or insert a bodily implant (not shown) into a body of a patient. In some embodiments, the medical device 100 is configured to be used to insert an implant into a body of a patient (e.g., a female patient, a male patient) using an inside-out approach (e.g., an inside-out approach via a vaginal incision in the body of the patient, an inside-out approach via a rectal incision in the body of the patient, or an inside-out approach via another bodily incision). The medical device 100 may be used to insert any type of implant into a body of a patient. In some embodiments, the medical device 100 can be configured to place an implant into a pelvic region of a patient. Specifically, in some embodiments, the medical device 100 is configured to place an implant through an obturator muscle and/or a membrane of a patient.

As shown in FIG. 1, the medical device 100 has an external arm 110 and an internal arm 120. The internal arm 120 is coupled (e.g., movably coupled, slidably coupled, rotatably coupled, hingedly coupled) to the external arm 110 so that the internal arm 120 and the external arm 110 can be moved towards one another. Specifically, in this embodiment, a proximal portion 122 of the internal arm 120 is rotatably coupled to a proximal portion 112 external arm 110 to collectively define a hinge portion 104 of the medical device 100. As shown in FIG. 1, the external arm 110 and the internal arm 120 are rotatably coupled (e.g., hingedly coupled using a pin, a screw, and/or so forth) about an axis E (coming out of the figure).

As shown in FIG. 1, the internal arm 120 can be moved (e.g., rotatably moved) in a direction A1 (e.g., a clockwise direction) toward the external arm 110 and/or the external arm 110 can be moved (e.g., rotatably moved) in a direction A2 (e.g., a counterclockwise direction) toward the internal arm 120 so that a distance between at least a portion of the external arm 110 and at least a portion of the internal arm 120 is decreased (e.g., decreased to approximately 3 inches (7.62 cm), decreased to less 4 inches (10.16 cm), decreased to less 2 inches (5.08 cm)). The internal arm 120 can be moved (e.g., rotatably moved) in the direction A2 (e.g., counterclockwise direction) away from the external arm 110 and/or the external arm 110 can be moved (e.g., rotatably moved) in the direction A1 (e.g., clockwise direction) away from the internal arm 120 so that a distance between at least a portion of the external arm 110 and at least a portion of the internal arm 120 is increased (e.g., in some embodiments, the distance is increased to greater than 1.5 inches (3.81 cm), increased to greater 2 inches (5.08 cm), increased to greater 4 inches (10.16 cm), and/or increased to approximately 5 inches (12.7 cm)).

In the embodiment shown in FIG. 1, the medical device 100 is in an open configuration. The medical device 100 can be moved from the open configuration to a clamped configuration (or closed configuration) by moving the external arm 110 toward the internal arm 120 (or vice versa). After being moved to the clamped configuration, the medical device 100 can be moved from the clamped configuration (or closed configuration) to the open configuration by moving the internal arm 120 away from the external arm 110 (or vice versa).

As shown in FIG. 1, the internal arm 120 includes (or is movably coupled to) a sliding component 140 configured to slidably move along a guide 130 (which can be referred to as a guide portion, or as a guide portion of the internal arm 120) of the internal arm 120. The sliding component 140 includes, or is coupled to, a needle 160 configured to slidably move within the guide 130. In some embodiments, the needle 160 can have a distal portion 162, and the distal portion 162 can have a distal tip 164. The sliding component 140 is configured to slidably move in direction B1 along the guide 130 so that the distal portion 162 of the needle 160 is moved toward the external arm 110. The sliding component 140 is also configured to slidably move in direction B2 (for example, after being moved in direction B1) along the guide 130 so that the distal portion 162 of the needle 160 is moved away from the external arm 110. In some embodiments, the guide 130 can define a channel or groove (with sidewalls) within which the needle 160 and/or the sliding component 140 may slidably move.

The external arm 110 includes a receiving mechanism 170 on a distal portion 114 the external arm 110. In some embodiments, the receiving mechanism 170 can be, or can include, an opening, a cavity, a slot, a hook, a latch, a recess, and/or so forth. In some embodiments, the slot can be, for example, an L-shaped slot or a T-shaped slot.

At least a portion of an implant (e.g., the tether of the implant, association members of the implant) (not shown) is configured to be inserted into a body of a patient and can be coupled to the distal portion 162 of the needle 160. In some embodiments, the portion of the implant coupled to the distal portion 162 of the needle 160 may not remain inside of the body of the patient after the procedure to place the implant within the body is completed. In some embodiments, the portion of the implant coupled to the distal portion 162 of the needle 160 may be separated from (e.g., decoupled from, cut from) a portion of the implant (e.g., a sling portion) that remains inside of the body of the patient.

The sliding component 140 (and needle 160) as illustrated in FIG. 1, is in a stowed configuration. The sliding component 140 (and needle 160) can be moved from the stowed configuration to a deployed configuration (not shown) when the sliding component 140 is moved in direction B1 along the guide 130. The sliding component 140 can be moved from the deployed configuration to the stowed configuration by slidably moving the sliding component 140 in direction B2 along the guide 130. In such embodiments, when the sliding component 140 is moved in direction B2 along the guide 130, the distal portion 162 of the needle 160 is moved away from the external arm 110.

When in the stowed configuration, a distal portion 162 of the needle 160 is disposed within (e.g., in a position disposed within) the internal arm 120 and/or the guide 130, or is in a position proximal to the distal end 125 of the internal arm 120. When in the deployed configuration, the distal portion 162 of the needle 160 is moved outside of (e.g. is moved to position outside of) the internal arm 120 (and/or the guide 130) so that at least a portion of the distal portion 162 of the needle 160 is distal to or extends from the distal end 125 of the internal arm 120. In some embodiments, the stowed configuration can be referred to as a retracted configuration, and the deployed configuration can be referred to as an extended configuration.

In some embodiments, the sliding component 140 (and needle 160) can have many different deployed configurations and/or stowed configurations. For example, the sliding component 140 (and needle 160) can be moved along direction B1 from a first deployed configuration to a second deployed configuration. A portion of the needle 160 disposed outside of the guide 130, when in the first deployed configuration, can be shorter than a portion of the needle 160 disposed outside of the guide 130 when the sliding component 140 is in the second deployed configuration. In some embodiments, the sliding component 140 (and the needle 160) can be moved along direction B2 from the second deployed configuration to the first deployed configuration.

In some embodiments, the guide 130 can have a portion that defines a lumen within which the needle 160 can be disposed and/or slidably moved. For example, although not shown in FIG. 1, the guide 130 can define a portion that extends between sidewalls of a channel or groove of the guide 130. The portion can be configured to prevent (or substantially prevent) the needle 160 from moving (e.g., sliding) out of the guide 130 when the needle 160 is slidably moved within the guide 130. An example of a guide that has a portion that defines at least a portion of a lumen is described, for example, in connection with FIGS. 3 and 5.

The sliding component 140 (and needle 160) can be configured so that the sliding opponent 140 can be moved between stowed configurations and/or deployed configurations when the medical device 100 is in the clamped configuration (or closed configuration) or the open configuration. For example, the medical device 100 can be moved from an open configuration to a clamped configuration, while the sliding component 140 is in a stowed configuration. After the internal arm 120 is moved toward the external arm 110 along direction A1 (or the external arm 110 is moved toward the internal arm 120 along direction A2) so that the medical device 100 is in the clamped configuration, the sliding component 140 (and needle 160) can be slidably moved along direction B1 from the stowed configuration to a deployed configuration. As another example, the medical device 100 can be moved from a clamped configuration to an open configuration while the sliding component 140 is in a deployed configuration. After the internal arm 120 is moved away from the external arm 110 along direction A2 so that the medical device 100 is in the open configuration, the sliding component 140 (and needle 160) can be slidably moved along direction B2 from the deployed configuration to a stowed configuration.

In some embodiments, when the sliding component 140 is in the deployed configuration, at least a portion of the needle 160 (e.g., the distal portion 162 of the needle 160) can contact, or can be moved into relatively close proximity, to at least a portion of the external arm 110. In some embodiments, when the sliding component 140 is in the deployed configuration, at least a portion of the needle 160 can contact and/or can be moved inside of at least a portion of the receiving mechanism 170 of the external arm 110. For example, if the receiving mechanism 170 defines, or includes, a cavity, at least a portion of the needle 160 can be moved inside of the cavity when the sliding component 140 is in the deployed configuration.

In some embodiments, when the sliding component 140 is in the deployed configuration, at least a portion of an implant can be coupled to the needle 160 (e.g., at least a portion of the distal portion 162 of the needle 160). Specifically, the needle 160 can have a coupling mechanism 166 at a distal portion 162 of the needle 160 to which at least a portion of an implant can be coupled. In some embodiments, the coupling mechanism 166 can be, or can include, an opening, a slot, a hook, a latch, a recess, and/or so forth. In some embodiments, the slot can be, for example, an L-shaped slot or a T-shaped slot. After the portion of the implant has been coupled to the needle 160, the portion of the implant can be moved into the receiving mechanism 170 of the external arm 110.

In some embodiments, operation of the medical device 100 is as follows. The sliding component 140 can be moved to the deployed configuration, while the medical device 100 is in the open configuration, so that the coupling mechanism 166 of the needle 160 may be moved out of the guide 130 (and/or a lumen of the guide 130). A portion of an implant may be coupled to the coupling mechanism 166 of the needle 160 while the sliding component 140 is in the deployed configuration and the medical device 100 is in the open configuration. After the portion of the implant has been coupled to the coupling mechanism 166 of the needle 160, the sliding component 140 can be moved to the stowed configuration so that the portion of the implant (that is coupled to the coupling mechanism 166 of the needle 160) may be refracted into the guide 130. The medical device 100 can be moved to the clamped configuration and the sliding component 140 can be moved to the deployed configuration so that the portion of the implant may be moved into (or near) the receiving mechanism 170 of the external arm 110 where the portion of the implant may be decoupled from the coupling mechanism 166 of the needle 160. In some embodiments, the coupling mechanism 166 of the needle 160 can be actuated, or triggered to be actuated, so that the implant may be coupled or decoupled from the coupling mechanism 166.

In some embodiments, the distal tip 164 of the needle 160 can be configured to cut or pierce a bodily tissue. For example, in some embodiments, the distal tip 164 can include a sharp portion. In some embodiments, the distal tip 164 can define a blunt end. In some embodiments, the distal tip 164 can define a dilating end configured to dilate a tissue of a patient.

As mentioned above, in some embodiments, the medical device 100 may be used to insert an implant (e.g., a surgical implant) (not shown) into a pelvic region of a patient. Specifically, the medical device 100 can be used to insert an implant into a pelvic region of a patient using an inside-out method. A specific example is set forth below.

First, a portion of the implant (e.g., the tether of the implant, association members of the implant) can be coupled to, or associated with, the coupling mechanism 166 of the needle 160 of the medical device 100. In some embodiments, the portion of the implant can be coupled to, or associated with, the coupling mechanism 166 of the needle 160 of the medical device 100 when the medical device 100 is in the open configuration and when the sliding mechanism 140 is in a deployed configuration (where the coupling mechanism 166 of the needle 160 is exposed (e.g., outside of the guide 130 and/or a lumen of the guide 130)). An example of an implant that can be used with the medical device 100 is shown in connection with FIG. 3.

After the portion of the implant has been coupled to, or associated with, the coupling mechanism 166 of the needle 160, the sliding mechanism 140 can be moved from the deployed configuration to the stowed configuration so that the coupling mechanism 166 (and the distal tip 164) of the needle 160, and the portion of the implant coupled thereto, may be retracted into the internal arm 120 of the medical device 100. The coupling mechanism 166 (and the distal tip 164) of the needle 160 may be retracted into the internal arm 120 of the medical device 100 so that the coupling mechanism 166 (and the distal tip 164) of the needle 160 may not come in contact with a tissue of a patient as the internal arm 120 of the medical device 100 is inserted into a body of the patient. Also, the coupling mechanism 166 (and the distal tip 164) of the needle 160, and the portion of the implant coupled thereto, may be retracted into the internal arm 120 medical device 100 so that the portion of the implant coupled to the coupling mechanism 166 may not become decoupled from the coupling mechanism 166 as the internal arm 120 of the medical device 100 is inserted into a body of a patient.

After the portion of the implant has been coupled to, or associated with, the coupling mechanism 166 of the needle 160 (and the coupling mechanism 166 of the needle 160 has been retracted), the internal arm 120 of the medical device 100 (e.g., at least a portion of the distal portion 124 of the internal arm 120) can be inserted into a body of a patient. In some embodiments, the internal arm 120 of the medical device 100 may be inserted into the pelvic region of the patient through an anterior vaginal incision (i.e., via an inside-out approach). In some embodiments, the medical device 100 can be inserted into the body of the patient such that the internal arm 120 is moved along an edge of, or in close proximity to, an edge of a bone (e.g., a pelvic bone) of the patient.

In some embodiments, the medical device 100 can be in the open configuration (or moved to the open configuration) shown in FIG. 1 when at least the distal portion 124 (and coupling mechanism 166 of the needle 160 which is coupled to or associated with the portion of the implant) of the internal arm 120 of the medical device 100 is inserted into the body of the patient. Specifically, the medical device 100 can be in the open configuration shown in FIG. 1 so that the external arm 110 may remain outside of (e.g., may be disposed outside of) the body of the patient (e.g., outside of a skin of the patient).

After the internal arm 120 has been inserted into the body of the patient, the medical device 100 can be moved to the clamped configuration. Specifically, the external arm 110 and the internal arm 120 can be moved toward one another so that a distance between, for example, the guide 130 and the receiving mechanism 170 may be decreased. When moved to the clamped configuration, the receiving mechanism 170 of the external arm 110 of the medical device 100 may come in contact with the body of the patient. In some embodiments, the receiving mechanism 170 of the external arm 110 may compress a tissue (e.g., a skin tissue) of the patient. In some embodiments, a physician may apply a force (along direction A2) to the external arm 110 so that the medical device 100 can be changed to the clamped configuration.

In some embodiments, the medical device 100 may be placed in a desirable location with respect to, for example an obturator muscle and/or another target membrane of a patient before being moved to the clamped configuration. Specifically, the medical device 100 may be placed so that the guide 130 (or at least a portion thereof) and the coupling mechanism 166 of the needle 160 (which is coupled to or associated with the portion of the implant) may be disposed on one side of an obturator muscle (and/or another target membrane) of the patient and the receiving mechanism 170 may be disposed on another side of the obturator muscle (and/or another target membrane) of the patient. Accordingly, when the sliding component 140 is moved to the deployed configuration, the distal tip 164 of the needle 160 will be slidably moved through the guide 130 and pierce through the obturator muscle (and/or another target membrane) of the patient and toward the receiving mechanism 170.

After the medical device 100 (e.g., the external arm 110 and the internal arm 120) is in a clamped configuration in a desirable location around, for example, the obturator muscle (and/or another target membrane) of the patient, the sliding component 140 can be moved from the stowed configuration to the deployed configuration (along direction B1) so that the distal tip 164 of the needle 160 can be deployed (e.g., extended out of the guide 130) and pierce through the obturator muscle (and/or another target membrane). The distal tip 164 of the needle 160 may be moved until the coupling mechanism 166, which is coupled to at least a portion of the implant (e.g., a tether of the implant, association members of the implant) is moved into, or in close proximity to, the receiving mechanism 170 of the external arm 110. Specifically, the distal tip 164 the needle 160 may be moved using the sliding component 140 until the coupling mechanism 166, and at least a portion of the implant coupled thereto, may be moved outside of body of patient and into, or in close proximity to, the receiving mechanism 170 of the external arm 110 so that the portion of the implant may be retrieved by, for example, a physician.

During a medical procedure, the coupling mechanism 166, and a portion of the implant coupled thereto, may not be visible to a physician using the medical device 100 after the internal arm 120 has been inserted into the body of the patient. Even though the internal arm 110 (and the portion of the implant coupled thereto) may not be visible to the physician using the medical device 100 when the sliding component 140 is moved to the deployed configuration, the guide 130 may be configured so that the coupling mechanism 166 of the needle 160 may be received at the receiving mechanism 170 disposed outside of a body of the patient in a desirable fashion.

In some embodiments, the receiving mechanism 170 can be used (e.g., used as a target) to determine a precise or an approximate location that the distal tip 164 of the needle 160 will pierce through a skin tissue of a patient (from inside the body of the patient to outside of the body of the patient) as the needle 160 is deployed using the sliding mechanism 140. In other words, the receiving mechanism 170 of the external arm 110 can be used to determine a precise or an approximate location where the needle 160 (and an implant portion coupled thereto) may be moved out of the body of the patient. Said another way, the receiving mechanism 170 can be used as an indicator of a precise or an approximate location that the needle 160 may pierce through and exit a skin tissue of the body of the patient.

In some embodiments, the receiving mechanism 170 of the external arm 110 can be aligned with the needle 160 and/or the sliding component 140 so that the distal portion 162 (e.g., distal tip 164) of the needle 160 will come into close proximity to (or will be inserted into) the receiving mechanism 170 over a range of positions of (or regardless of the position of) the receiving mechanism 170 with respect to the sliding component 140 and/or the needle 160. For example, the receiving mechanism 170 (and the external arm 110) can be configured so that distal tip 164 of the needle 160 may be moved into the receiving mechanism 170 when the medical device 100 is in the clamped configuration (or a set/range of clamped configurations) and/or when the medical device 100 is in the open configuration (or a set/range of open configurations). In some embodiments, the receiving mechanism 170 (and the external arm 110) can also be configured so that distal tip 164 of the needle 160 may be moved into the receiving mechanism 170 when the medical device 100 is in a configuration between the clamped configuration and the open configuration.

As mentioned above, the distal tip 164 of the needle 160 can be moved, using the sliding component 140, until the coupling mechanism 166, and at least a portion of the implant coupled thereto, are moved outside of the body of the patient and into, or close proximity to, the receiving mechanism 170 of the external arm 110. After the distal tip 164 the needle 160 is moved, using the sliding component 140, until the coupling mechanism 166, and at least a portion of the implant coupled thereto, are moved outside of body of patient, the portion of the implant may be retrieved by, for example, a physician. In such embodiments, the portion of the implant can be decoupled (e.g., extracted) from the coupling mechanism 166 of the needle 160. Thus, the portion of the implant can be decoupled from (e.g., extracted from, removed from) the coupling mechanism 166 by, for example, a physician after the sliding component 140 is moved to the deployed configuration.

After the portion of the implant is decoupled from the coupling mechanism 166 of the needle 160, the sliding component 140 can be moved in direction B2 from the deployed configuration to a stowed configuration so that the internal arm 120 may be withdrawn from the body of the patient (without interference from the needle 160). In other words, the coupling mechanism 166 of the needle 160 can be retracted, after being decoupled from the implant (or at least a portion thereof).

Although the portion of the implant is withdrawn from body of the patient, another portion of the implant (e.g., a sling portion of the implant) may remain within the body of the patient. In some embodiments, the portion of the implant withdrawn from the body of the patient may be used to adjust a location and/or tension of the portion of the implant remaining within the body of the patient. In some embodiments, the portion of the implant coupled to the distal portion 162 of the needle 160 may be separated from (e.g., decoupled from, cut from) a portion of the implant (e.g., a sling portion) that remains inside of the body of the patient.

In some embodiments, the process described above for inserting one or more implants (or a portions thereof) can be performed on one side of a body of a patient and on another side of the body of the patient. For example, a first tether of an implant can be inserted through an obturator foramen on a first side of a body of a patient using the medical device 100. Subsequently, a second tether of the implant can be inserted through an obturator foramen on a second side of the body of the patient using the medical device 100 (or another medical device the same as or similar to medical device 100). Examples of implants implanted into different sides of a body of a patient using, for example, medical device 100 are shown in FIG. 6B. In some embodiments, the process described above for inserting one or more implants (or portions thereof) can be performed multiple times on the same side of a body of a patient. In some embodiments, different implant portions (associated with separate implants) can be inserted into different portions (e.g., different sides) of a body of a patient using one or more medical device such as medical device 100.

Because certain tissues of a patient (e.g., an obturator muscle) can be relatively stiff and/or relatively difficult to pierce, the guide 130 of the internal arm 120 can function as a support for the needle 160 as the distal tip 164 is moved through the tissue(s). Specifically, the guide 130 of the internal arm 120 can be made of a relatively rigid material that can prevent (or substantially prevent) the needle 160 from bending in an undesirable fashion. In some embodiments, the guide 130 can support the needle 160 while the distal tip 164 is moved through a tissue so that the needle 160 may not be deformed inelastically. Because the distal end of the guide 130 can be contacting, or close to, tissue that will be pierced by at least a portion of the distal tip 164 of the needle 160, a length of the portion of the distal portion 162 can be relatively small (e.g., a few millimeters), or nearly zero, when the distal tip 164 contacts the tissue as the sliding mechanism 140 is moved to the deployed configuration.

The guide 130 is configured so that the sliding component 140 can be slidably moved along the guide 130. In some embodiments, the guide 130 can be, or can include, a slot or groove or channel into which the sliding component 140 can be inserted and slidably moved. In some embodiments, the guide 130 can include a member (e.g., a rod) along which the sliding component 140 can slidably move. In some embodiments, at least a portion of the sliding component 140 can be disposed around (e.g., at least partially around), or otherwise coupled to, the member. In some embodiments, the sliding component 140 and/or the guide 130 can include rolling devices such as wheels or ball-bearings that can facilitate translational movement (e.g., facilitate relatively smooth translational movement) of the sliding component 140 along the guide 130. A cross-sectional view of an example of a portion of a guide is shown and described in connection with FIG. 3B.

In some embodiments, the needle 160 has a circular cross-sectional shape (or outer profile). In some embodiments, the needle 160 can have a different shape than a circular cross-sectional shape. In some embodiments, the needle 160 can have a cross-sectional shape (or outer profile) of any type of polygon. For example, the needle 160 can have a square or a rectangular cross-sectional shape (or outer profile). In some embodiments, the needle 160 can have a tapered shaped and/or a tapered portion (e.g., tapered from a proximal portion to a distal portion). In such embodiments, the needle 160 can have a varying diameter.

In some embodiments, the guide 130 can have a cross-sectional shape of any type of polygon. For example, the guide 130 can have a square or rectangular cross-sectional shape (or outer profile) within which the needle 160 can be disposed. In some embodiments, the guide 130 can have a tapered shaped and/or a tapered portion (e.g., tapered from a proximal portion to a distal portion).

In some embodiments, the needle 160 has a portion of a surface with a cross-sectional shape (or outer profile) that matches a portion of an inner surface of the guide 130. In some embodiments, the needle 160 can have a shape that does not match (e.g., is different from) a cross-sectional shape of the guide 130.

As shown in FIG. 1, internal arm 120 has a radius R of curvature that is approximately the same as a radius S of curvature of the external arm 110. In some embodiments, the radius R of curvature of the internal arm 120 can be different than the radius S of curvature of the external arm 110. For example, the radius S of curvature of the external arm 110 can be greater than the radius R of curvature of the internal arm 120.

As shown in FIG. 1, the external arm 110 and the internal arm 120 both define a semi-circle. In some embodiments, the internal arm 120 and/or the external arm 110 can have different shapes than those shown in FIG. 1. For example, in some embodiments, the external arm 110 and/or the internal arm 120 can have a curved shape that is not a semi-circle. Also, in some embodiments, the external arm 110 and/or the internal arm 120 may not have a curved shape. Additional examples of shapes of external arms and internal arms are described below.

As shown in FIG. 1, the external arm 110 can be aligned along an axis Q1 from a distal tip 172 (or distal portion) of the receiving mechanism 170 through the axis E, and the internal arm 120 can be aligned along an axis Q2 from the distal tip 125 (or distal portion) through the axis E. As shown in FIG. 1, an acute angle is defined by the axis Q2 of internal arm 120 and the axis Q1 of external arm 110 when the medical device 100 is in the open configuration. A second acute angle, that is smaller than the first acute angle, is defined by the axis Q2 of internal arm 120 and the axis Q1 of the external arm 110 when the internal arm 120 is moved towards the external arm 110 to define the clamped configuration of the medical device 100. Thus, an angle between axis Q2 of the internal arm 120 and the axis Q1 of the external arm 110 decreases when the medical device 100 is moved from the open configuration to the clamped configuration. It follows that the angle between axis Q2 of the internal arm 120 and the axis Q1 of the external arm 110 increases when the medical device 100 is moved from the clamped configuration to the open configuration. Thus, the medical device 100 can be reversibly moved to/from the clamped configuration or the open configuration.

Although not shown in FIG. 1, in some embodiments, the medical device 100 can have one or more locking mechanisms configured to removably (e.g., releasably) lock the medical device 100 into one or more clamped configurations and/or one or more open configurations. In some embodiments, the medical device 100 can also have one or more locking mechanisms configured to removably lock the sliding component 140 into one or more stowed configurations and/or one or more deployed configurations along the guide 130. More details related to locking mechanisms are discussed in connection with, for example, FIGS. 3A, 3D, and 5.

In some embodiments, movement of the sliding component 140 along the guide 130 may be limited based on a position of the external arm 110 with respect to the internal arm 120. For example, the movement of the sliding component 140 along the guide 130 may be limited to a particular position along the guide 130 when the medical device 100 is in a particular clamped configuration. More details related to movement of a sliding component being limited are discussed in connection with, for example, FIG. 5.

In some embodiments, the medical device 100 can include an indicator mechanism configured to indicate a position of at least a portion of the external arm 110 with respect to a portion of the internal arm 120. For example, the medical device 100 can include an indicator mechanism configured to indicate that the distal tip 164 of the needle 160 is disposed within the receiving mechanism 170 when the sliding component 140 is in a specified position along the guide 130. As another example, medical device 100 can include an indicator mechanism configured to represent a distance (e.g., relative distance) between at least a portion of the external arm 110 (e.g., the receiving mechanism 170 of the external arm 110) and at least a portion of the internal arm 120 (e.g., a distal portion of the guide 130). In some embodiments, because the distal portion 162 of the needle 160 of the internal arm 120, and an implant coupled thereto, may not be visible to the physician when using the medical device 100, the medical device 100 can include one or more indicators (and/or indicator mechanisms) configured to assist a physician in inserting the implant into a body of a patient in a desirable fashion. More details related to indicators are described in connection with, for example, FIG. 5.

Although not shown in FIG. 1, in some embodiments, the medical device 100 can be configured so that the medical device 100 is biased towards an open configuration (such as the open configuration shown in FIG. 1) or biased towards a clamped configuration. In such embodiments, a biasing mechanism such as a spring mechanism, a gear mechanism, and/or so forth, can be disposed between external arm 110 (or a portion thereof) and internal arm 120 (or portion thereof) to cause the medical device 100 to be biased toward one or more open configurations and/or one or more clamped configurations. In some embodiments, the biasing mechanism can be coupled to the medical device 100 at, or around, the hinge portion 104.

If biased toward the open configuration, a force (e.g., a constant force) may be applied (e.g., applied against the external arm 110 and/or the internal arm 120) to move the external arm 110 and the internal arm 120 towards one another so that the medical device 100 can be changed to the clamped configuration. When the force is no longer applied, the external arm 110 and the internal arm 120 can be moved away from one another by the biasing mechanism.

If biased towards the clamped configuration, a force (e.g., a constant force) may be applied (e.g., applied against the external arm 110 and/or the internal arm 120) to move the external arm 110 in the internal arm 120 away from one another so that the medical device 100 can be changed to the open configuration. When the force is no longer applied, the external arm 110 and the internal arm 120 can be moved towards one another in response to the biasing mechanism.

Although not shown in FIG. 1, in some embodiments, the sliding component 140 can be configured so that the sliding component 140 is biased toward a stowed configuration (such as the stowed configuration shown in FIG. 1) or a deployed configuration In such embodiments, a biasing mechanism such as a spring mechanism, a gear mechanism, and/or so forth, can be coupled to the guide 130, the sliding component 140, and/or so forth. As a specific example, the spring may be disposed between the sliding component 140 and the guide 150 to cause the sliding component 140 to be biased towards the stowed configuration shown in FIG. 1.

If biased towards the stowed configuration, a force (e.g., a constant force) may be applied (e.g., applied against the sliding component 140) to move the sliding component 140 along direction B1 along the guide 130 so that the sliding component 140 can be changed to the deployed configuration. When the force is no longer applied, the sliding component 140 can be moved back to the stowed configuration by the biasing mechanism. Similarly, if biased towards the deployed configuration, a force (e.g., a constant force) may be applied (e.g., applied against the sliding component 140) to move the sliding component 140 along direction B2 along the guide 130 so that the sliding component 140 can be changed to the stowed configuration. When the force is no longer applied, the sliding component 140 can be moved back to the deployed configuration by the biasing mechanism.

In some embodiments, at least a portion of the needle 160 can be formed of a flexible material. For example, a portion of the needle 160 that remains disposed within the guide 130 when in the stowed configuration and in the deployed configuration can be configured to flex or bend. In some embodiments, at least a portion of the needle 160 that is made of a flexible material can be biased to a specified position and/or curvature. In some embodiments, at least a portion of the needle 160 can be formed of a flexible material so that a portion of the needle 160 can conform to a curvature of the guide 130 (e.g., a varying curvature), if curved, as the needle 160 is slidably moved within the guide 130.

The medical device 100, or portions thereof, can be made of various types of materials such as a polymer-based material (e.g., a polycarbonate material), a metal (e.g., stainless steel), and/or so forth. In some embodiments, any portion of the medical device 100 can be formed of a biocompatible material. In some embodiments, needle 160 can be formed of, for example, a polymer-based material, a stainless steel material (e.g., surgical grade stainless steel), and/or so forth.

Figure 2:
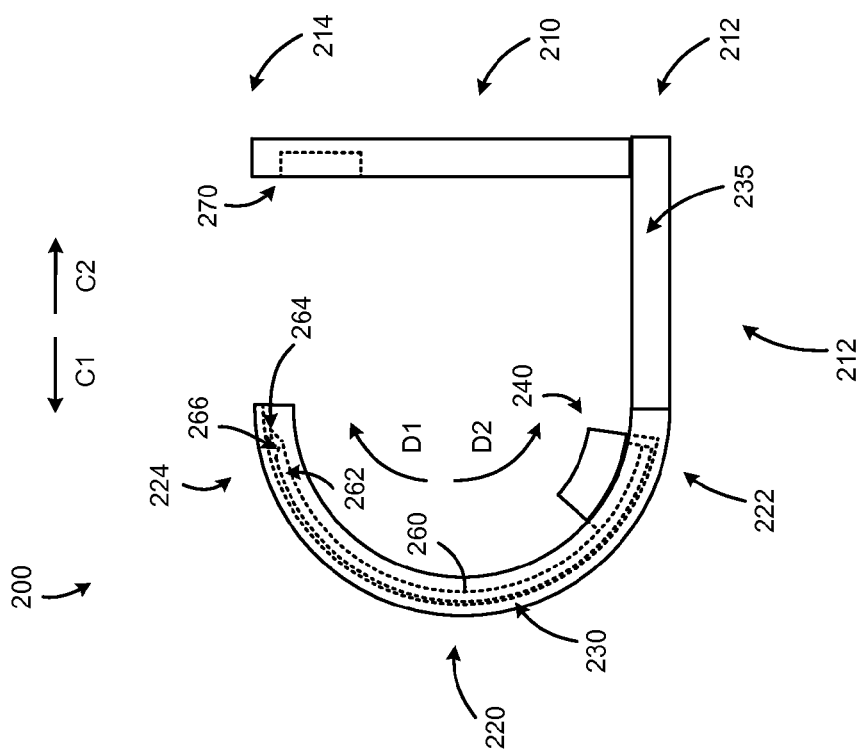
FIG. 2 is a schematic diagram of another medical device, according to an embodiment.

FIG. 2 is a schematic diagram of another medical device 200, according to an embodiment. The medical device 200 is configured to be used as an insertion tool or delivery tool to implant or insert a bodily implant (not shown) into a body of a patient (e.g., using an outside-in approach via a vaginal incision in the body of the patient).

As shown in FIG. 2, the medical device 200 has an external arm 210 coupled to an internal arm 220. The internal arm 220 can be moved (e.g., slidably moved) with respect to the external arm 210 in a direction C1 and/or a direction C2 along a guide 235 of the external arm 210. The guide 235 can be similar to the guides described above. The medical device 200 shown in FIG. 2 is in an open configuration, in some embodiments, the medical device 200 can also be moved to a clamped configuration.

Although the guide 235 is shown as being included in (or associated with) the external arm 210, in some embodiments, the guide 235 can be included in (or associated with) the internal arm 220. In some embodiments, the guide 235 can be a separate component (e.g., a guide component, a separate arm) along which both the external arm 210 and the internal arm 220 can be moved (e.g., slidably moved). In such embodiments, the external arm 210 and the internal arm 220 can be independently moved along the guide 235. In some embodiments, the internal arm 220 can be hingedly coupled to the guide 235.

Also, as shown in FIG. 2, a sliding component 240 may be slidably moved along a guide 230 (e.g., a guide associated with the sliding component 240) in the direction D1 (towards a receiving mechanism 270) and/or the direction D2 (away from the receiving mechanism 270). The sliding component 240 is shown in a stowed configuration in FIG. 2 (where a distal portion 262 of the needle 260 is disposed within the guide 230). In some embodiments, the sliding component 240 may also be moved to a deployed configuration. The sliding component 240 is coupled to (or includes) the needle 260 that is configured to slidably move within the guide 230.

Medical device 200 shown in FIG. 2 can include any of the features described in connection with and/or shown in the medical devices above. For example, medical device 200 can include one or more locking mechanisms, indicator mechanisms, ratchet mechanisms, syringes, and/or so forth.

In some embodiments, the sliding component 240 can be slidably moved along the guide 230 using a device configured to apply a force to the sliding component 240. For example, sliding component 240 can be moved along direction C1 and/or direction C2 using a motor. In some embodiments, the motor can be installed inside of the sliding component 240 and can be actuated by physician using a button coupled to the medical device. In some embodiments, the sliding component 240 can be slidably moved along the guide 230 using, for example, a ball-screw mechanism (not shown) coupled to a motor. Similarly, the external arm 210 and/or the internal arm 220 can be moved toward one another using a device configured to apply a force to the external arm 210 and/or the internal arm 220. One or more of the medical devices described above or below can incorporate a device (e.g., a motor) configured to slidably move a sliding mechanism and/or rotatably move portions of the medical devices.

Figure 3A:
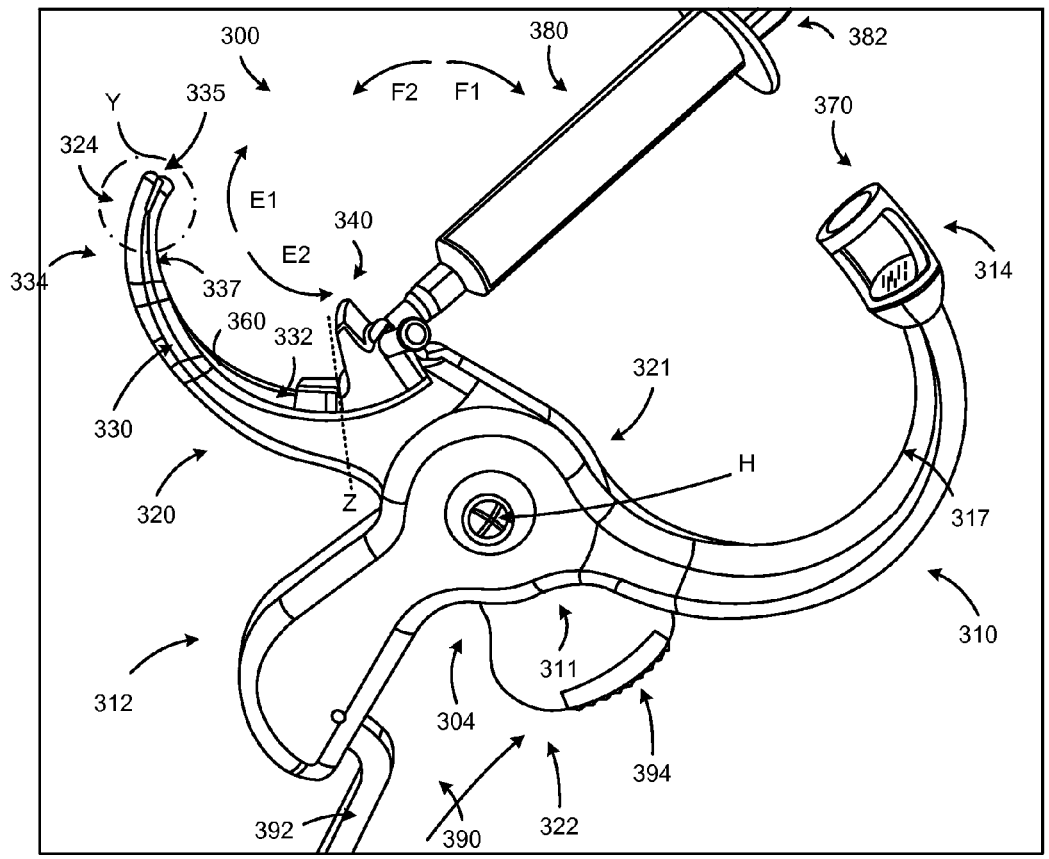
FIG. 3A is a side view of a medical device in an open configuration.

FIG. 3A is a side view of a medical device 300 in an open configuration. The medical device 300 is configured to be used as an insertion tool or delivery tool to implant or insert a bodily implant (not shown) into a body of a patient. In some embodiments, the medical device 300 is configured to be used to insert an implant into a body of a patient (e.g., a male patient, a female patient) using an inside-out approach (e.g., an inside-out approach via a vaginal incision in the body of the patient). The medical device 300 may be used to insert any type of implant into a body of a patient. In some embodiments, the medical device 300 can be configured to place an implant into a pelvic region of a patient. Specifically, in some embodiments, the medical device 300 is configured to place an implant through an obturator muscle and/or a membrane of a patient.

As shown in FIG. 3A, the medical device 300 has an external arm 310 and an internal arm 320. The internal arm 320 is coupled (e.g., rotatably coupled, hingedly coupled) to the external arm 310 so that the internal arm 320 and the external arm 310 can be moved towards one another. Specifically, a portion 321 (also can be referred to as a medial portion) of the internal arm 320 is rotatably coupled to a portion 311 (also can be referred to as a medial portion) of the external arm 310 to collectively define a hinge portion 304 of the medical device 300. In this embodiment, at least a portion of the portion 321 of the internal arm 320 is disposed inside of (and coupled to) the portion 311 of the external arm 310. Specifically, at least a portion of the portion 321 of the internal arm 320 is rotatably coupled to the portion 311 of the external arm 310. In some embodiments, at least a portion of the portion 311 of the external arm 310 may be disposed inside of the internal arm 320. In some embodiments, a portion of the internal arm 320 may not be disposed within a portion of the external arm 310.

As shown in FIG. 3A, the internal arm 320 can be moved (e.g., rotatably moved) in a clockwise direction F1 towards the external arm 310 and/or the external arm 310 can be moved (e.g., rotatably moved) in a counterclockwise direction F2 towards from the internal arm 320 so that a distance between at least a portion of the external arm 310 (e.g., a receiving mechanism 370 of the external arm 210) and at least a portion of the internal arm 320 (e.g., a guide 330 of the internal arm 320) is decreased. The internal arm 320 can be moved (e.g., rotatably moved) in a counterclockwise direction F2 away from the external arm 310 and/or the external arm 310 can be moved (e.g., rotatably moved) in a clockwise direction F1 away from the internal arm 320 so that a distance between at least a portion of the external arm 310 (e.g., the receiving mechanism 370 of the external arm 310) and at least a portion of the internal arm 320 (e.g., the guide 330 of the internal arm 320) is increased. As shown in FIG. 3A, the external arm 310 and the internal arm 320 are hingedly coupled (e.g., hingedly coupled using a pin, a screw, and/or so forth) about an axis H (coming out of the figure).

Figures 3B, 3C:
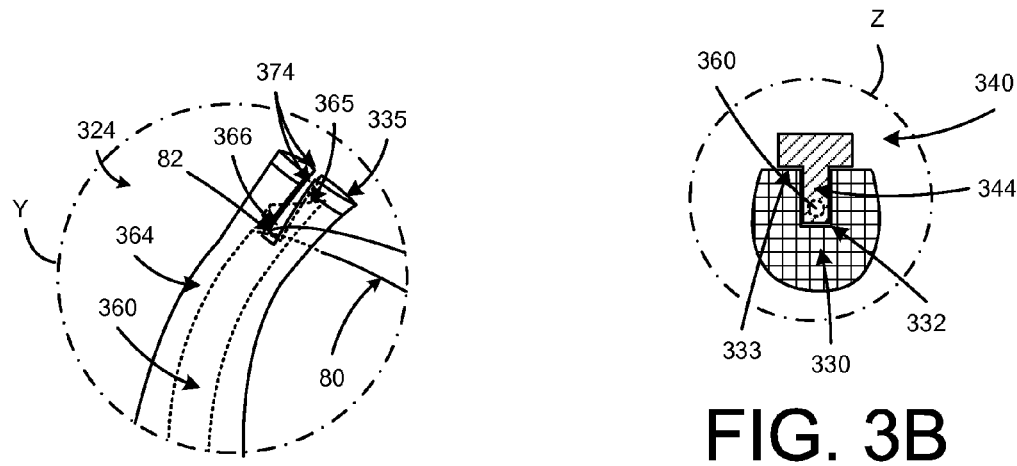
FIG. 3B is a cross-sectional view of a sliding component and a guide of the medical device shown in FIG. 3A taken along line Z of FIG. 3A.
FIG. 3C is a zoomed in view of a distal portion of an internal arm of the medical device shown in FIG. 3A.
Figure 3D:
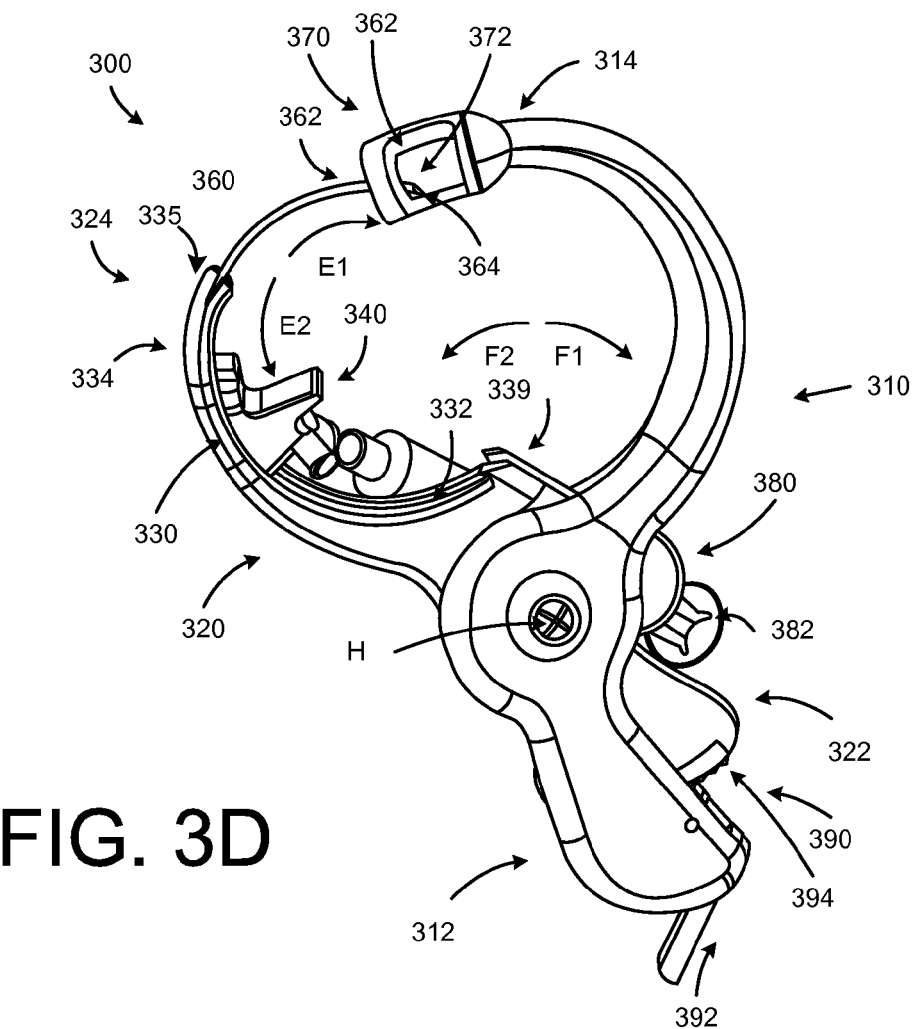
FIG. 3D is a side view of the medical device shown in FIG. 3A in a clamped configuration.

FIG. 3D is a side view of the medical device 300 shown in FIG. 3A in a clamped configuration. The medical device 300 can be moved from the open configuration shown in FIG. 3A to a clamped configuration shown in FIG. 3D by moving the external arm 310 toward the internal arm 320 (and/or vice versa). In some embodiments, the medical device 300 can be moved to the clamped configuration shown in FIG. 3D after at least a portion of the internal arm 320 has been inserted into a body of a patient (e.g., into a vaginal region of the patient) while the medical device 300 is in the open configuration shown in FIG. 3A. In some embodiments, a distal portion of (e.g., a left portion of) the receiving mechanism 370 may be pushed against (e.g., compressed against) a tissue (e.g., a skin layer) of the patient when the medical device 300 is moved to the clamped configuration after the portion of the internal arm 320 has been inserted into the body of the patient. After being moved to the clamped configuration, the medical device 300 can be moved from the clamped configuration (shown in FIG. 3D) to the open configuration (shown in FIG. 3A) by moving the external arm 310 away from the internal arm 320 (and/or vice versa).

As shown in FIG. 3D, a distal portion 324 of the internal arm 320 includes a sliding component 340 configured to slidably move along the guide 330 (which can be referred to as a guide portion) of the internal arm 320. The sliding component 340 is coupled to (or includes) a needle 360 configured to slidably move within the guide 330. In some embodiments, the needle 360 can have a distal portion 362 and the distal portion 362 can have a distal tip 364. The sliding component 340 is configured to slidably move in direction E1 along the guide 330 so that the distal portion 362 of the needle 360 (and sliding component 340) is moved into at least a portion of the receiving mechanism 370. The sliding component 340 is also configured to slidably move in direction E2 (after being moved in direction E1) the distal portion 362 of the needle 360 (and sliding component 340) is moved away from the receiving mechanism 370.

As shown in FIG. 3A, the guide 330 has a groove 332 (also can be referred to as a channel) along which at least a portion of the sliding component 340 slidably moves. Also, as shown in FIG. 3A, a distal portion of the guide 330 (e.g., the distal portion 324 of the internal arm 320) defines at least a portion of a lumen 335 within which at least a portion of the needle 360 may slidably move. In this embodiment, the portion of the guide 330 that defines the lumen 335 can be referred to as a lumen portion 334 of the guide 330. Thus, the guide 330 can have a lumen portion (i.e., lumen portion 334) and a grooved portion (corresponding with the groove 332).

The movement of the sliding component 340 is limited when the sliding component 340 is at an end of the groove 332, which is at, or is approximately, the point at which the lumen portion 334 of the guide 330 begins. As shown in FIG. 3D, the movement of the sliding component 340 is prevented from moving beyond the end of the groove 332 because the sliding component 340 (e.g., a front end of the sliding component 340) is at the lumen portion 334 of the guide 330. In some embodiments, the sliding component 340 can have a protrusion (e.g., a tab) (not shown) that limits (e.g., stops) the movement of the sliding component 340 when the protrusion comes into contact with the end of the groove 332. Also as shown in FIG. 3D, the guide 330 can have a stop 339 that prevents the sliding component 340 from being slidably moved off of the guide 330 along direction E2.

In some embodiments, the receiving mechanism 370 of the external arm 310 can be aligned with the needle 360 and/or the sliding component 340 so that the distal portion 362 (e.g., distal tip 364) of the needle 360 will come into close proximity to (or will be inserted into) the receiving mechanism 370 when the medical device 300 is in a clamped configuration (or when the external arm 310 is in a range of positions with respect to the internal arm 320). For example, the receiving mechanism 370 (and the external arm 310) can be configured so that distal tip 364 of the needle 360 may be moved into the receiving mechanism 370 when the medical device 300 is in the clamped configuration as shown in FIG. 3D, or in a different clamped configuration than that shown in FIG. 3D. In some embodiments, the receiving mechanism 370 (and the external arm 310) can also be configured so that distal tip 364 of the needle 360 may be moved into the receiving mechanism 370 when the medical device 300 is in a configuration between the clamped configuration and the open configuration.

As shown in FIGS. 3A and 3D, the external arm 310 and the internal arm 320 each have a sickle shape. In this embodiment, at least a portion of an inner surface 337 of the concave portion of the guide 330 faces towards at least a portion of the receiving mechanism 370 of the medical device 300. Likewise, at least a portion of an inner surface 317 of the concave portion of the external arm 310 faces towards at least a portion of the distal portion 324 of the internal arm 320.

In this embodiment, at least a portion of the proximal portion 312 of the external arm 310 and a portion of the proximal portion 322 of the internal arm 320 collectively define a handle portion of the medical device 300 when the medical device 300 is in the clamped configuration (shown in FIG. 3D). When in the open configuration shown in FIG. 3A, at least a portion of the proximal portion 312 of the external arm 310 can define the handle portion of the medical device 300.

FIG. 3B is a cross-sectional view of the sliding component 340 and the guide 330 shown in FIG. 3A. Specifically, the cross-sectional view shown in FIG. 3B is cut along the line Z (shown in FIG. 3A). In this embodiment, the sliding component 340 includes a portion 344 disposed within a groove 332 of the guide 330 so that the sliding component 340 may remain coupled to (e.g., may not become decoupled from) the guide 330. The guide 330 has a top surface 333 along which the sliding component 340 can slidably move. In some embodiments, the top surface 333 of the guide 330 can be a curved surface, a flat surface, and/or so forth. In some embodiments, the guide 330 can have a cross-sectional shape (or outer profile) of any type of polygon. For example, the guide 330 can have a square or a rectangular cross-sectional shape (or outer profile). In some embodiments, the guide 330 can have a tapered shaped and/or a tapered portion (e.g., tapered from a proximal portion to a distal portion).

As shown in FIGS. 3A and 3D, the internal arm 320 (and external arm 310), the sliding component 340, and the needle 360 can be configured to move within a plane that is orthogonal to, or substantially orthogonal to, the axis H. The needle 360 can be disposed within the plane. In some embodiments, the radius of curvature of the guide 330 and/or of the needle 360 can be between, for example, 2.0 inches (5.08 centimeters (cm)) and 20 inches (50.8 cm) (e.g., 10 inches (24.5 cm), 5 inches (12.7 cm)). In some embodiments, the radius of curvature of the guide 330 and/or of the needle 360 can be less than 2.0 inches (5.08 cm), or can be greater than 20 inches (50.8 cm).

In some embodiments, an implant portion configured to be inserted into a body of a patient can be coupled to the distal portion 364 of the needle 360. In some embodiments, the implant portion can be, for example, a tether (or other type of association member) coupled to a sling portion of an implant. A zoomed in view (area Y) of the distal portion 324 of the internal arm 320 when the distal portion 364 of the needle 360 is coupled to an implant portion 80 is shown in FIG. 3C. The implant portion 80 is not shown in FIG. 3A.

FIG. 3C illustrates the distal portion 324 of the internal arm 320 shown in FIG. 3A. As shown in FIG. 3C, the distal portion 324 of the internal arm 320 includes slots 374 into which the implant portion 80 may be inserted when (or either after or before) the implant portion 80 is coupled to a coupling mechanism 366 of the distal portion 364 of the needle 360. As shown in FIG. 3C the distal portion 364 of the needle 360 is in a stowed configuration and retracted into a lumen of 335 a lumen portion 334 of the guide 330 of the internal arm 320. In some embodiments, the lumen portion 334 can be referred to as a lumen of the guide 330. When the implant portion 80 is inserted into the slots 374, a portion 82 of the implant portion 80 spans between the slots 374. In some embodiments, the slots 374 can be sized so that the implant portion 80 may be press fit into one or more of the slots 374. Although not shown in FIG. 3C, in some embodiments, the coupling mechanism 366 can also be, or can include, a hook, a latch, and/or so forth.

In some embodiments, the implant portion 80 may be coupled to the coupling mechanism 366 of the distal portion 364 of the needle 360 when the sliding component 340 is in a deployed configuration and the needle 360 is disposed outside of the guide 330. After the implant portion 80 has been coupled to the coupling mechanism 366 of the distal portion 364 of the needle 360, the sliding component 340 can be moved to the stowed configuration (from the deployed configuration) and the needle 360, and the implant portion 80 coupled thereto, can be retracted into the guide 330. The needle 360, and the implant portion 80 coupled thereto, can be retracted into the guide 330 so that the internal arm 320 may be inserted into a body of the patient without being obstructed by the needle 360, and the implant portion 80 coupled thereto. When the sliding component 340 is once again moved to the deployed configuration, the implant portion 80 may be slidably moved within, and out of, the guide 330 (e.g., the lumen 335 of the guide 330).

In some embodiments, the implant portion 80 may be coupled to the coupling mechanism 366 of the needle 360 while the sliding component 340 is in the deployed configuration and the needle 360 is disposed inside of the guide 330. In such embodiments, the implant portion 80 may be moved into the slots 374 until the implant portion 80 is moved into the coupling mechanism 366 of the needle 360. In such embodiments, the portion 82 of the implant portion 80 may be deflected upward and/or the distal end portion 362 of the needle 360 may be deflected downward as the distal surface 365 of the needle 360 comes into contact with (e.g., contacts, slides along) the portion 82 of the implant portion 80.

In some embodiments, the implant portion 80 may be coupled to the coupling mechanism 366 of the needle 360 as the sliding component 340 is being moved from a stowed configuration to a deployed configuration. In such embodiments, the implant portion 80 may be inserted into the slots 374 of the distal portion 324 of the internal arm 320 so that the portion 82 of the implant portion 80 spans the slots 374. In some embodiments, the slots 274 can be sized so that the implant portion 80 may be press fit into one or more of the slots 274. After the implant portion 80 is inserted into the slots 374, the sliding component 340 may be in a stowed configuration such that the distal surface 365 of the needle 360 is proximal to the portion 82 of the implant portion 80 that spans the slots 374. The distal tip 364, the distal portion 362 of the needle 360 can be moved along direction E1 by the sliding component 340 toward the deployed configuration so that the distal tip 364 moves below the implant portion 80. The portion 82 of the implant portion 80 that spans the slots 374 may contact a distal surface 365 of the needle 360 as the distal tip 364 and the portion of the distal portion 362 are moved out of the lumen 335 of the guide 330. The portion 82 of the implant portion 80 may be moved along the distal surface 365 until the portion 82 of the implant portion 80 is coupled with (e.g., moved into, engaged with) the coupling mechanism 366 of the needle 360. In some embodiments, the coupling mechanism 366 can be, or can include, an opening, a slot, a hook, a latch, a recess, and/or so forth. In some embodiments, the slot can be, for example, an L-shaped slot or a T-shaped slot. In some embodiments, the portion 82 of the implant portion 80 may be deflected upward and/or the distal end portion 362 of the needle 360 may be deflected downward as the distal surface 365 of the needle 360 comes into contact with (e.g., contacts, slides along) the portion 82 of the implant portion 80.

Referring back to FIG. 3A, the receiving mechanism 370 is included in a distal portion 314 of the external arm 310. Specifically, the receiving mechanism 370 is included at the end of a curved portion of the external arm 310. In some embodiments, the receiving mechanism 370 may be included on a different portion of the external arm 310 such as a medial portion of the external arm 310.

The sliding component 340 (and needle 360) as illustrated in FIG. 3A, is in a stowed configuration. The sliding component 340 can be moved from the stowed configuration (shown in FIG. 3A) to a deployed configuration, shown in FIG. 3D, when the sliding component 340 is moved in direction E1 along the guide 330 (and through the lumen portion 334 of the guide 330). The sliding component 340 can be moved from the deployed configuration (shown in FIG. 3D) to the stowed configuration (shown in FIG. 3A) by slidably moving the sliding component 340 in direction E2 along the guide 330.

When in the stowed configuration shown in FIG. 3A, a distal portion 362 of the needle 360 is disposed within (e.g., in a position disposed within) the lumen portion 334 of the guide 330 or is in a position proximal to the guide 330. When in the deployed configuration shown in FIG. 3D, the distal portion 362 of the needle 360 is moved outside of (e.g. is moved to position outside of) the lumen portion 334 of the guide 330 so that the distal portion 362 of the needle 360 is distal to the guide 330. In this embodiment, the sliding component 340 is slidably moved along the guide 330 so that the sliding component 340 is in the deployed configuration shown in FIG. 3D after the medical device 300 is moved to the clamped configuration (e.g., after the distal portion 324 of the internal arm 320 is moved towards the distal portion 314 of the external arm 310).

In some embodiments, when the sliding component 340 is moved to the deployed configuration, the distal tip 364 of the needle 360 will be slidably moved through the lumen 335 of the guide 330 and will pierce a tissue of a patient (for example, if the internal arm 320 of the medical device 300 is disposed within a body of the patient). For example, the distal tip 364 of the needle 360 can be configured to pierce through a skin tissue (from the inside), an obturator muscle, and/or another target membrane of the patient and toward the receiving mechanism 370 of the external arm 310.

In this embodiment, when the sliding component 340 is in the deployed configuration shown in FIG. 3D, the distal tip 364, and at least a portion of the distal portion 362, of the needle 360 is moved into a portion 373 of the receiving mechanism 370. The distal tip 364 is moved into the portion 373 of the receiving mechanism 370 so that an implant portion coupled to the coupling mechanism 366 of the needle 360 may be decoupled from (e.g., removed from, disengaged from) the coupling mechanism 366 of the needle 360. A zoomed in view of the coupling mechanism 366 of the needle 360 disposed within the receiving mechanism 370 of the external arm 310 is shown in FIG. 3E.

Figure 3E:
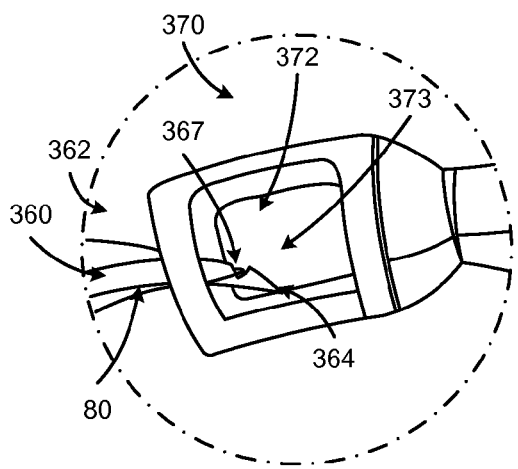
FIG. 3E is a zoomed in view of a needle disposed within a receiving mechanism of the external arm of the medical device shown in FIG. 3A.

As shown in FIG. 3E, in this embodiment, the coupling mechanism 366 is a slot 367 into which the implant portion 80 can be coupled when the distal tip 364, and at least a portion of the distal portion 362 of the needle 360 is moved into the portion 373 of the receiving mechanism 370. Specifically, the distal tip 364 and the coupling mechanism 366 (which can be coupled to the implant portion) of the needle 360 can be moved along direction E1 into the receiving mechanism 370. After the distal tip 364 is moved into the portion 373 of the receiving mechanism 370 the implant portion 80 coupled to the coupling mechanism 366 of the needle 360 can be decoupled from (e.g., removed from, disengaged from) the coupling mechanism 366 of the needle 360 by a physician through an opening 372 of the coupling mechanism. In some embodiments, the coupling mechanism 366 can be, or can include, an opening, a slot, a hook, a latch, a recess, and/or so forth. In some embodiments, the slot can be, for example, an L-shaped slot or a T-shaped slot. After an implant portion has been decoupled from the needle 360, the sliding component 340 may be moved along direction E2 until the sliding component 340 is in a stowed configuration, and the internal arm 320 can be removed from the body of the patient.

As shown in FIG. 3E, the receiving mechanism 370 can have more than one opening (such as opening 372) through which the implant portion 80 can be retrieved from the distal portion 362 of the needle 360. In some embodiments, the receiving mechanism 370 can have only one opening through which the implant portion 80 can be retrieved from the distal portion 362 of the needle 360. In some embodiments, the opening 372 can have any shape, such as a circular shape, a rectangular shape, and/or so forth.

During a medical procedure, the receiving mechanism 370 of the external arm 310 (and the implant portion coupled thereto) may not be visible to a physician using the medical device 300 when the needle 360 (e.g., the distal portion 362 of the needle 360) of the internal arm 320 (and the implant portion coupled thereto) are disposed within a body of a patient. Even though the distal portion 362 of the needle 360 of the internal arm 320 (and the implant portion coupled thereto) may not be visible to the physician using the medical device 300 when the sliding component 340 is moved to the deployed configuration, the guide 330 may be configured so that the distal tip 364 and the portion of the distal portion 362 may be moved into the receiving mechanism 370 in a desirable fashion. In some embodiments, the needle 360 may be configured (e.g., configured with a stiffness) so that the distal tip 364 of the needle 360, and the portion of the distal portion 362, will be moved into the receiving mechanism 370 without deflecting in an undesirable fashion.

In some embodiments, the receiving mechanism 370 of the external arm 310 can be used to determine a precise or an approximate location where the needle 360 (and an implant portion coupled thereto) may be moved out of the body of the patient. In other words, the receiving mechanism 370 can be used as an indicator of a precise or an approximate location that the distal tip 362 of the distal portion 364 of the needle 360 may pierce through and exit a skin tissue of the body of the patient.

Although not shown, in some embodiments, as the sliding component 340 is moved along direction E2, at least a portion of an implant portion coupled to the needle 360 may be moved to a desirable position with the body of the patient by the needle 360 and the sliding component 340. In such embodiments, the implant portion can be released from the needle 360 (using an actuating mechanism) so that the implant portion may be placed within the body of the patient.

Because the guide 330 (and lumen portion 334) can function as a support for the needle 360, the needle 360 can have a cross-sectional area (along a plane orthogonal (or approximately orthogonal) to a longitudinal axis of the needle 360) that is smaller than would otherwise be permissible without the guide 330. In other words, the needle 360 can be relatively thin (e.g., can have a relatively small diameter) because only a relatively short portion of the needle 360 may project from the guide 330 when the sliding component 340 is in the deployed configuration. In some embodiments, the diameter of the needle 360 can be less than 3 millimeters (mm). For example, in some embodiments, the needle 360 can have a diameter of approximately 2.5 mm. In some embodiments, the needle 360 can have a diameter less than 2.5 mm or a diameter greater than 2.5 mm. Also, because the guide 330 can function as a support for the needle 360, the needle 360 can have a curvature that is greater than (e.g., has a smaller radius of curvature) would otherwise be permissible without the guide 330. In some embodiments, the receiving mechanism 370 of the external arm 310 can be moved so that the receiving mechanism 370 is contacting, or is relatively close to (e.g., less than 2 mm, less than 2 cm), a tissue through which at least a portion of the needle 360 is to pierce (on the opposite side).

In some embodiments, the needle 360 can define a lumen that is configured to convey fluids to and/or from a body of a patient. As shown in FIGS. 3A and 3D the sliding component 340 of the medical device 300 has a proximal portion 342 configured to be coupled to a fluid delivery device such as syringe 380. In this embodiment, the proximal portion 342 of the sliding component 340 is a manifold that defines two openings through which a fluid delivery device may deliver fluid to, or remove fluid from, a lumen defined by the needle 360. An opening of the portion proximal 342 can be in fluid communication with the lumen of the needle 360 so that a fluid can be delivered from the fluid delivery device via the proximal portion 342 and into the lumen of the needle 360. In some embodiments, the proximal portion 342 of the sliding component 340 may not be a manifold, but may instead define a single opening through which a fluid delivery device may deliver fluid to, or remove fluid from, a lumen defined by the needle 360.

In this embodiment, the syringe 380 is configured to deliver a fluid to and/or draw a fluid from the needle 360. In some embodiments, the syringe 380 is a 30 cc syringe. In other embodiments, the syringe 380 is larger or smaller than 30 cc. In some embodiments, a device other than a syringe may be used to move a liquid through the needle 360.

In this embodiment, the syringe 380 is coupled to the sliding component 340 in a relatively rigid fashion so that the syringe 380 may be used by a physician to move the sliding component 340. In other words, the medical device 300 may be configured so that a physician can slidably move the sliding component 340 along the guide 330 by applying a force (e.g., a pulling force, a pushing force) to the syringe 380. In some embodiments, the medical device 300 may be configured so that a physician can push and/or pull a plunger 382 of the syringe 380 (while moving the sliding component 340) to deliver and/or withdraw, respectively, a fluid from the lumen of the needle 360. Thus, a fluid may be delivered and/or withdrawn via the needle 360 while the sliding component 340 is in, or moving to, the stowed configuration and/or is in, or moving to, the deployed configuration. In some embodiments, the fluid may be delivered and/or withdrawn via the needle 360 while the medical device 300 is in, or moving to, the clamped configuration and/or is in, or moving to, the open configuration.

In some embodiments, for example, a lumen defined by the needle 360 may be used to deliver medication or anesthesia to the body of the patient during the procedure to place an implant within the body of the patient. In some embodiments, the lumen may be used to help hydro-dissect the bodily tissue during an implantation procedure. The lumen defined by the needle 360 may be of any shape or size. For example, the cross-sectional shape (or outer profile) of the lumen may be circular, square, or rectangular.

Figure 5:
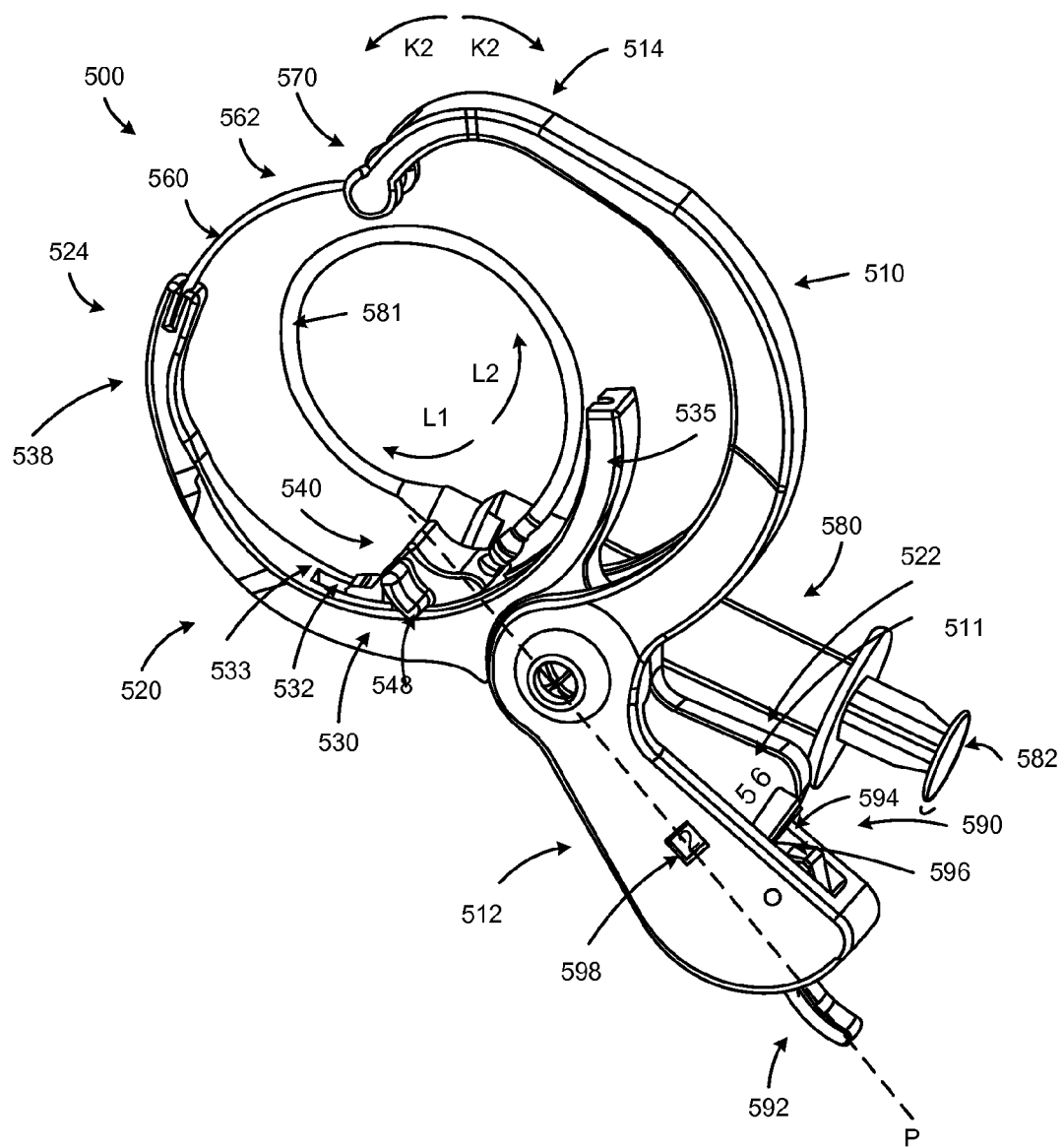
FIG. 5 illustrates yet another medical device according to an embodiment.

Although not shown in FIG. 3A, a tube, tether, or other device configured to convey a fluid can be disposed between the sliding component 340 and the syringe 380. In other words, the syringe 380 can be configured to deliver a fluid via a tube to the sliding component 340. In such embodiments, the sliding mechanism 340 can be operated by a first person (e.g., a first physician) and the syringe 380 can be operated by a second person (e.g., a second physician or an assistant). An example of such a configuration is shown in FIG. 5.

As shown in FIG. 3A, the medical device 300 has a locking mechanism 390 configured to lockably couple the internal arm 320 with respect to the external arm 310. In other words, locking mechanism 390 can be used to releasably lock the medical device 300 in one or more open configurations and/or one or more clamped configurations. As shown in FIG. 3A, at least a first portion of locking mechanism 390 is included in (e.g., coupled to, disposed within) the external arm 310 and at least a second portion of the locking mechanism 390 is included in (e.g., coupled to, disposed within) the internal arm 320. In some embodiments, at least a portion of locking mechanism 390 may not be disposed inside of the external arm 310 and/or the internal arm 320.

In this embodiment, the locking mechanism 390 has protrusions 394 (e.g., teeth, latches) (not shown) that can be used to be coupled to (e.g., contact, catch on) one or more protrusions (e.g., teeth, gear teeth) (not shown) included in the internal arm 320. The protrusions 394, when coupled to the protrusion(s) of the external arm 310, can releasably lock a position of the external arm 310 with respect to a position of the internal arm 320.

As shown in FIG. 3A, the locking mechanism 390 has a control lever 392 (when pushed and/or pulled by a physician) that can be used to trigger the locking mechanism 390 to releasably lock the medical device 300 in one or more open configurations and/or one or more clamped configurations. The control lever 392 (when pushed and/or pulled by a physician) can also be configured to release the medical device 300 from one or more releasably locked configurations.

Although not shown in FIG. 3A, in some embodiments, movement of the external arm 310 can be limited with respect to the internal arm 320. For example, movement of the external arm 310 can be limited so that the external arm 310, or a portion thereof (e.g., the receiving mechanism 370), may not come in contact with the internal arm 320. In some embodiments, the movement of the external arm 310 can be limited with respect to the internal arm 320 by the locking mechanism 390 and/or a stop (not shown) disposed between the external arm 310 and the internal arm 320.

Although not shown in FIG. 3, the sliding component 340 can include a locking mechanism configured to releasably lock the sliding component 340 in a position along the guide 330. In some embodiments, the sliding component 340 can be releasably locked in any position along the guide 330 using a lever (e.g., a protrusion, a tab) (not shown). For example, the sliding component 340 can be releasably locked in the stowed configuration shown in FIG. 3A or the deployed configuration shown in FIG. 3D.

In some embodiments, a locking mechanism of the sliding component 340 can be biased so that the sliding component 340 may not be moved along the guide 330 unless a lever is actuated. In other words, the locking mechanism of the sliding component 340 can be configured so that the lever can be actuated to release the locking mechanism so that the sliding component 340 may be slidably moved along the guide 330. In some embodiments, the locking mechanism of the sliding component 340 can be biased so that the sliding component 340 may not be locked into a position along the guide 330 until actuated using the lever. In other words, the locking mechanism of the sliding component 340 can be configured so that the lever can be actuated to lock the sliding component 340 along the guide 330.

Figure 4:
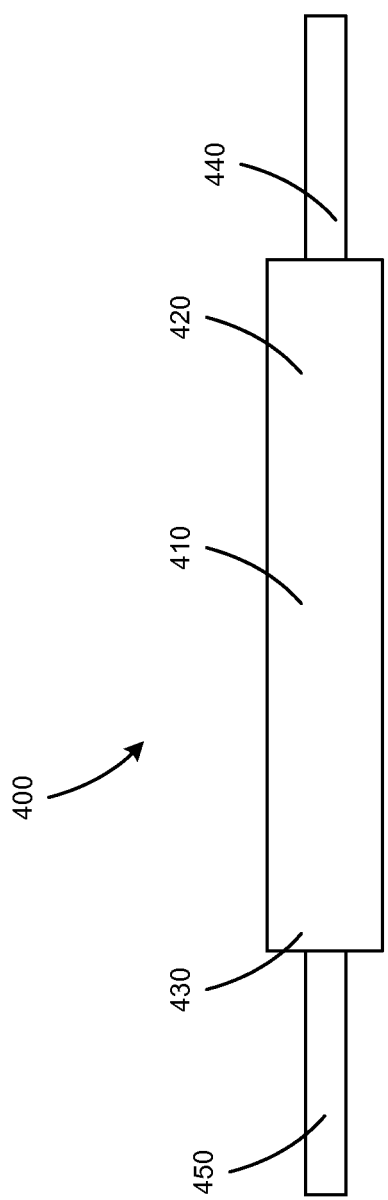
FIG. 4 is a schematic diagram of an implant according to an embodiment.

The medical devices described herein (e.g., the medical devices shown in FIGS. 1 through 3) may be used to insert an implant into a pelvic region of a patient. For example, an implant 400 as illustrated in FIG. 4 may be implanted into a pelvic region of a patient using the medical devices. The implant 400 shown in FIG. 4 is a sling and includes a support portion 410, end portions 420 and 430, and association members 440 and 450. In some embodiments, the association members 440, 450 can be tethers. The support portion 410 can be configured to be placed proximate a portion of the body of the patient and can be configured to provide support to the portion of the body. The end portions 430 and 440 can be configured to be placed into and coupled to bodily tissue to anchor the implant 400 within the body of the patient. The association members 440 and 450 can be configured to associate the implant 400 to the medical devices (e.g., a distal portion of a needle) during an implantation procedure.

In some embodiments, the implant 400 may be formed of any biocompatible material. In some embodiments, the implant 400 can be formed of a mesh material. For example, the implant 400 may be formed of Advantage® mesh or the Polyform™ synthetic mesh, both as produced and/or sold by Boston Scientific Corporation. In some embodiments, the implant 400 may be formed of a polymer material. In some embodiments, the material of the implant 400 allows for tissue in-growth to secure the implant 400 to the bodily tissue of the patient.

In some embodiments, the implant 400 can include tangs to help retain the implant 400 in place within the body of the patient. In such embodiments, the tang or tangs can be configured to engage the bodily tissue surrounding the implant 400 help retain the implant 400 in place within the body of the patient. The terms "tanged" or "tangs" as used herein mean roughened or jagged edges or areas, such as can result from cutting a woven or knit mesh material.

FIG. 5 illustrates yet another medical device 500, according to an embodiment. The medical device 500 is configured to be used as an insertion tool or delivery tool to implant or insert a bodily implant (not shown) into a body of a patient (e.g., using an inside-out approach via a vaginal incision in the body of the patient).

As shown in FIG. 5, the medical device 500 has an external arm 510 coupled (e.g., hingedly coupled, rotatably coupled) to an internal arm 520. The internal arm 520 can be moved (e.g., rotatably moved) with respect to the external arm 510 in a direction K1 and/or a direction K2. The medical device 500 shown in FIG. 5 is in a clamped configuration, in some embodiments, the medical device 500 can also be moved to an open configuration. In this embodiment, the external arm 510 of the medical device 500 has a medial portion hingedly coupled to a medial portion of the internal arm 520 of the medical device 500. In this embodiment, at least a portion of the proximal portion 512 of the external arm 510 and at least a portion of the proximal portion 522 of the internal arm 520 collectively define a handle portion 506 of the medical device 500.

As shown in FIG. 5, a sliding component 540 may be slidably moved along a guide 530 in direction L1 (towards a receiving mechanism 570) and/or direction L2 (away from the receiving mechanism 570). Also, as shown in FIG. 5, the sliding component 540 includes a tab 548 (also can be referred to as a protrusion) that can be used to push and/or pull the sliding component 540.

As shown in FIG. 5, the guide 530 has an extension portion 535 that extends beyond a longitudinal axis P, which is aligned along the handle portion 506 (or aligned along at least one of the proximal portion 522 of the internal arm 520 and the proximal portion 512 of the external arm) of the medical device 500. In other words, a portion of the guide 530 is disposed on one side of the longitudinal axis P, and the extension portion 535 of the guide 530 is disposed on another side of the longitudinal axis P. Accordingly, the sliding component 540 may be slidably moved from one side of the longitudinal axis P to another side of the longitudinal axis P.

As shown in FIG. 5, movement of the sliding component 540 is limited when the sliding component 540 is at an end 533 of the groove 532 (which also can be referred to as a channel). In some embodiments, the sliding component 540 can have a protrusion (e.g., a tab) (not shown) that limits (e.g., stops) the movement of the sliding component 540 when the protrusion comes into contact with the end 533 of the groove 532. The movement of the sliding component 540 may be limited so that the sliding component 540 will be prevented (or substantially prevented) from moving into a body of the patient when the distal portion 524 of the internal arm 520 is disposed within the body of the patient. As shown in FIG. 5, the guide 530 also has a lumen portion 538.

Because the medical device 500 has the extension portion 535 of the guide 530, the needle 560 can be configured with a length that is sufficient to move a portion of an implant coupled thereto into a desirable location within the body of the patient, or to a desirable location outside of the body of the patient. In other words, a range of translational movement of the sliding component 540 and of the needle 560 is longer than would otherwise be possible without the extension portion 535 of the guide 530.

As shown in FIG. 5, a tube 581 is configured to convey a fluid between the sliding component 540 and the syringe 580. In other words, the syringe 580 can be configured to deliver a fluid via the tube 581 to the sliding component 540. In such embodiments, the sliding mechanism 540 can be operated by a first person (e.g., a first physician) and the syringe 580 can be operated by a second person (e.g., a second physician).

The sliding component 540 is shown in a deployed configuration in FIG. 5. In some embodiments, the sliding component 540 may also be moved to a stowed configuration (where a distal portion 562 of the needle 560 is disposed within a lumen portion 538 of a guide 530). The sliding component 540 is coupled to (or includes a needle) 560 that is configured to slidably move within the lumen portion 538 of the guide 550.

In the embodiment shown in FIG. 5 the needle 560 of the medical device 500 is configured to convey a fluid. The needle 560 can define a lumen that is configured to convey fluids to and/or from a body of a patient. As shown in FIG. 5, the sliding component 540 is coupled to a syringe 580. The syringe 580 is configured to deliver a fluid (e.g., a medication or anesthesia) to and/or draw a fluid from the needle 560 (using a plunger 582).

As shown in FIG. 5, the medical device 500 has a locking mechanism 590 configured to lockably couple the internal arm 520 with respect to the external arm 510. In some embodiments, the locking mechanism 590 can be referred to as a ratchet mechanism. The locking mechanism 590 can be used to releasably lock the medical device 500 in one or more open configurations and/or one or more clamped configurations.

The internal arm 520 includes protrusions 594 (e.g., teeth) (on a distal portion 522) that can be configured to be coupled to (e.g., contact, catch on) protrusions 596 (not visible in FIG. 5) (e.g., teeth) disposed within the external arm 510 (and facing the protrusions 594). The protrusions 594, when coupled to (e.g., contacted with) the protrusions 596 of the external arm 510, can lock a position of the external arm 510 with respect to a position of the internal arm 520. The coupling of one or more of protrusions 594 to one or more of the protrusions 596 can be released using lever 592. Although not shown, in some embodiments, protrusions can be disposed within the internal arm 520. In such embodiments, protrusions can be included on the distal portion 512 of the external arm 510.

In some embodiments, the locking mechanism 590 can be biased so that the position of the external arm 510 is lockably coupled (e.g., automatically lockably coupled) with respect to a position of the internal arm 520 using the locking mechanism 590 when the external arm 510 is moved with respect to the internal arm 520. In other words, the protrusions 594 and/or the protrusions 596 can be biased (e.g., biased using a spring) to contact one another as the internal arm 520 and the external arm 510 are moved with respect to one another. In such embodiments, lockable coupling of the position of the external arm 510 with respect to the position of the internal arm 520 can be released using the lever 592. In some embodiments, the locking mechanism 590 can be biased so that the position of the external arm 510 is lockably coupled with respect to a position of the internal arm 520 in response to the lever being actuated. In other words, the locking mechanism 590 can be biased to an unlocked configuration. In such embodiments, the protrusions 594 and the protrusions 596 may not be biased (e.g., biased using a spring) away from one another and may not come into contact until activated using the lever 592.

As shown in FIG. 5, the locking mechanism 590 is defined by at least a portion (i.e., a proximal portion 522) of the internal arm 520, which is disposed within at least a portion (i.e., a proximal portion 512) of the external arm 510. In some embodiments, at least a portion of locking mechanism 590 may not be disposed inside of the external arm 510 and/or the internal arm 520.

As shown in FIG. 5, the proximal portion 522 of the internal arm 520 has a window 598 through which indicators 511 (e.g., numbers, marks, detents) included in the proximal portion 522 of the internal arm 520 may be seen. The indicators 511 and the window 598 can be configured so that one or more of the indicators 511 visible through the window 598 can be an indicator of, for example, a distance between at least a portion of the external arm 510 (e.g., the receiving mechanism 570) and at least a portion of the internal arm 520 (e.g., a distal portion of the guide 530). In some embodiments, one or more of the indicators 511 can be an indicator of a relative positions (when the medical device 500 is in an open configuration and/or a clamped configuration) of at least a portion of the external arm 510 and at least a portion of the internal arm 520.

Although not shown, in some embodiments, the sliding mechanism 540 and/or the guide 530 can include one or more indicators (e.g., numbers, marks, detents) of, for example, a distance between at least a portion of the sliding component 540 and/or needle 560 (e.g., the distal portion 562 of the needle 560) and at least a portion of the external arm 510 (e.g., the receiving mechanism 570). In other words, one or more of the indicators can be an indicator of a relative position (when in a stowed configuration and/or a deployed configuration) between at least a portion of the sliding component 540 and/or needle 560 (e.g., the distal portion 562 of the needle 560) and at least a portion of the external arm 510 (e.g., the receiving mechanism 570).

In some embodiments, the medical device 500 can be configured so that even when the internal arm 520 is inserted into a body of a patient, the sliding mechanism 540 may be located along the internal arm 520 in a position (e.g., in a position outside of the body of the patient) where the sliding mechanism 540 can be accessed and/or used to move (e.g., slidably move) the needle 560 (and/or an implant coupled thereto) within the guide 530 and into the body of the patient. In such embodiments, the sliding mechanism 540 and/or the guide 530 can include one or more indicators (e.g., numbers, marks, detents) of a relative location of the sliding component 540 and/or needle 560 (e.g., the distal portion 562 of the needle 560) with respect to the medical device 500 and/or at least a portion of the external arm 510 (e.g., the receiving mechanism 570).

In some embodiments, medical device 500 can include one or more electronic indicators (e.g., light emitting diode (LED) indicators coupled to electronic contacts and a power supply, liquid crystal display indicators triggered by a microprocessor). For example, the medical device 500 can include an electronic indicator configured to indicate a position of at least a portion of the external arm 510 (e.g., the receiving mechanism 570) with respect to at least a portion of the internal arm 520 (e.g., the guide 530, a distal portion of the guide 550). In some embodiments, the medical device 500 can include an electronic indicator configured to indicate a relative position between at least a portion of the sliding component 540 and/or needle 560 (e.g., the distal portion 562 of the needle 560) and at least a portion of the external arm 510 (e.g., the receiving mechanism 570).

Figure 6A:
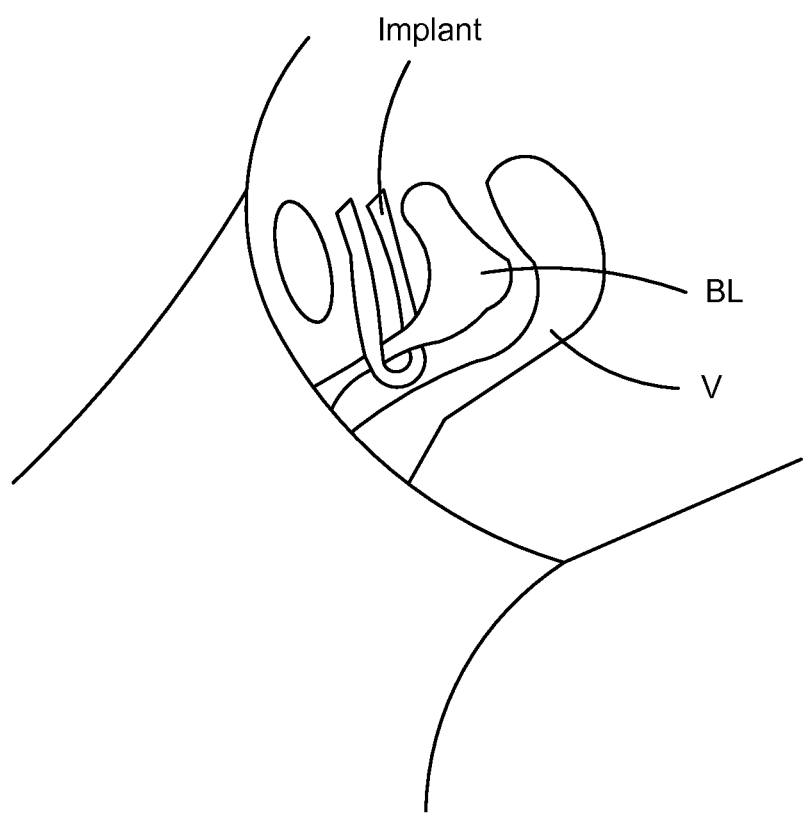
FIGS. 6A, 6B, and 6C schematically illustrate implants disposed within a body of a patient.
Figure 6B:
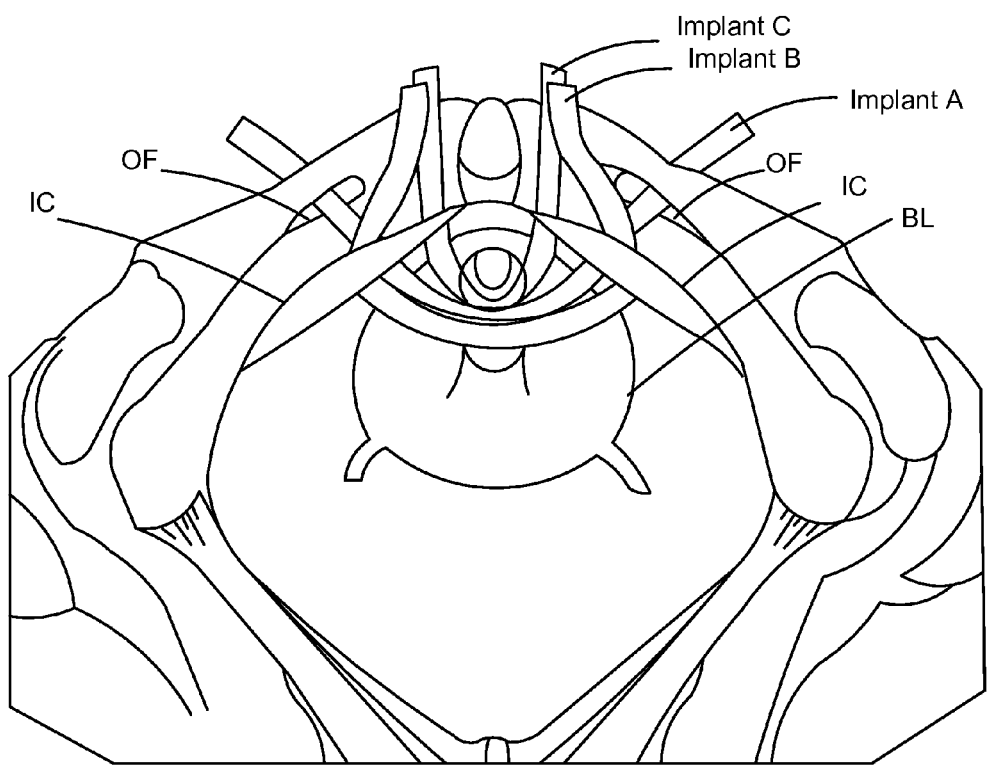

In some embodiments, as schematically illustrated in FIG. 6A, an implant (such as the implant 400 shown in FIG. 4) can be positioned, at least in part, by the medical devices described herein between a portion of a vagina V of a patient and a portion of a bladder BL of the patient such that the implant provides support to the bladder BL of the patient.

Figure 6C:
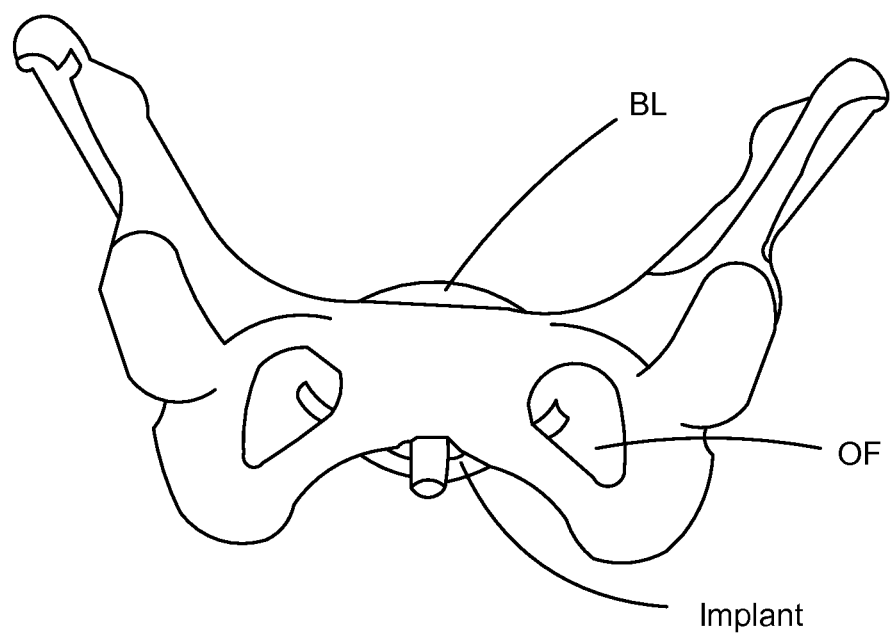

As illustrated in FIG. 6B, an implant (such as the implant 400 shown in FIG. 4) may be positioned, at least in part, by the medical devices described herein at different locations within the body of the patient. For example, as illustrated in FIG. 6B, implant A may be placed within the body of the patient such that the implant An extends through the obturator foramens OF of the patient. Alternatively, as illustrated, the implant B may extend between the midline incision, Ischiocavernosus muscle IC and in front of the pubic bone (prepubic approach). Alternatively, as illustrated, implant C may be disposed within the body of the patient in a "V" shape. Although not shown, in some embodiments, the implant B may extend between the ATFP (arcus tendineus facia pelvis) and the obturators of the patient As illustrated in FIG. 6C, an implant (such as the implant 400 shown in FIG. 4) may be placed, at least in part, by the medical devices described herein such that it extends toward the obturator foramens OF of the patient, but does not extend through the obturator foramens OF. For example, the implant may be disposed within or coupled to muscles disposed proximate the obturator foramens OF. In some embodiments, the implant may be decoupled from an end of a needle (after being retrieved from a coupling mechanism) of the medical device after being placed within a desirable location within the body of the patient using a decoupling mechanism (e.g., a latch mechanism, a decoupling mechanism at an end of the needle member) controlled using, for example, a lever, trigger, and/or so forth. In some embodiments, the medical devices described herein may be used to deliver an implant to the pelvic region of the patient via a retropubic (below) or a suprapubic (above) approach.

Figure 7:
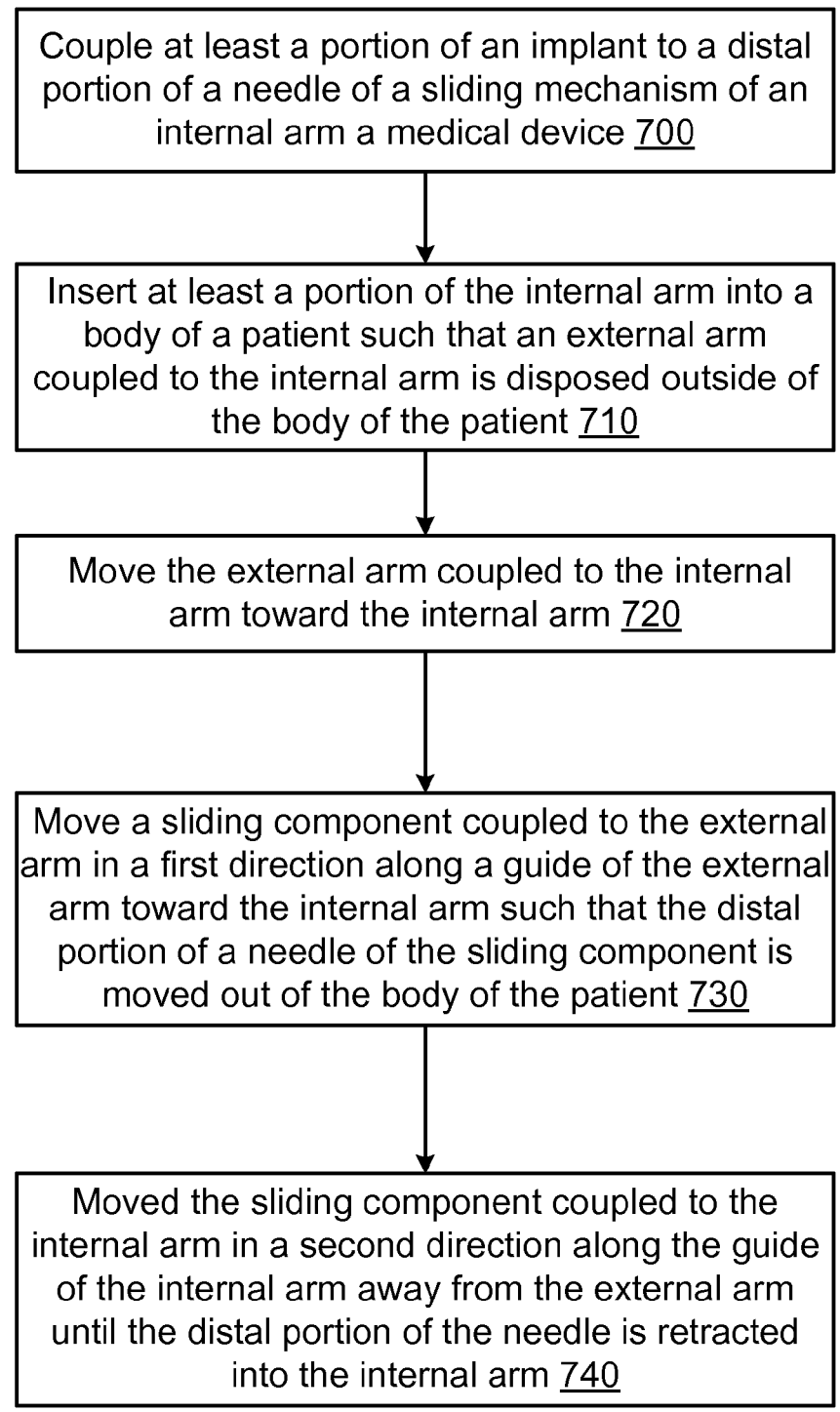
FIG. 7 is a flow diagram that illustrates a method for using a medical device.

FIG. 7 is a flow diagram that illustrates a method for using a medical device. In some embodiments, the medical device can be similar to, or the same as, the medical devices (e.g., medical device 100 shown in FIG. 1, medical device 200 shown in FIG. 2) described above.

At least a portion of an implant is coupled to a distal portion of a needle of the sliding mechanism of an internal arm of a medical device (block 700). In some embodiments, the portion of the implant can be, for example, a tether or suture of the implant. In some embodiments, the portion of the implant may be coupled to a coupling mechanism at a distal portion of the needle of the sliding mechanism when the sliding mechanism is in a deployed configuration so that the needle is moved outside of a guide (e.g., a lumen of the guide) of the internal arm. After the portion of the implant is coupled to the needle, the sliding mechanism may be moved to a stowed configuration so that the needle (and the portion of the implant coupled thereto) may be moved inside of the guide (e.g., a lumen of the guide) of the internal arm. In some embodiments, at least a portion of the implant may be moved into a slot of the internal arm.

Figure 8A:
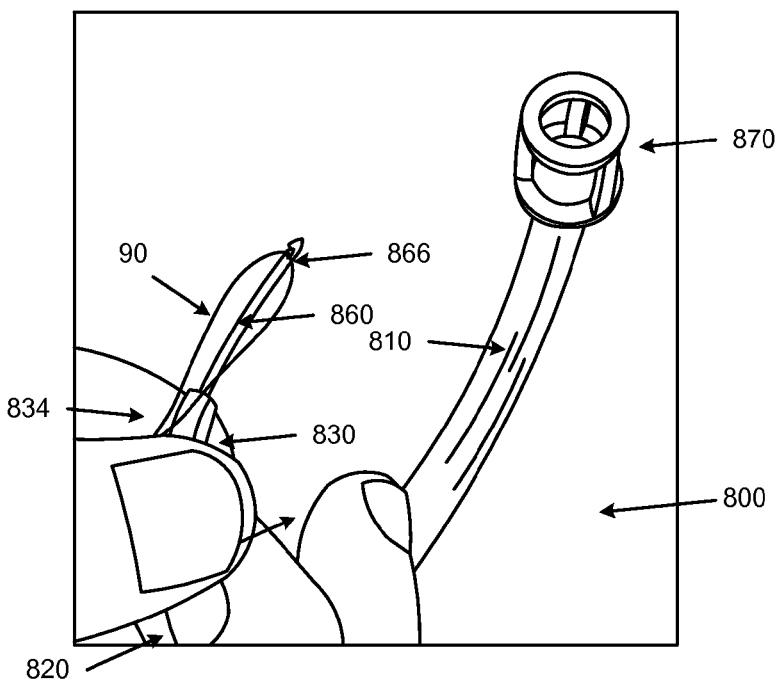
FIGS. 8A through 8G are diagrams that illustrate a method for using a medical device.
Figure 8B:
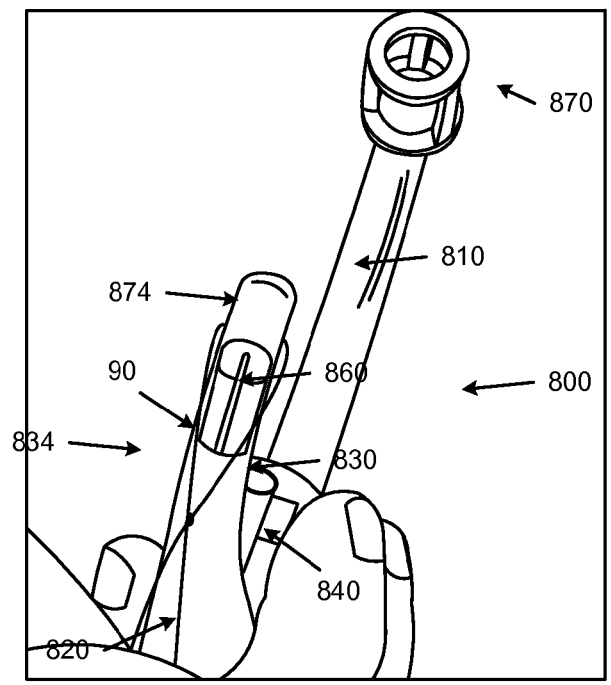

FIG. 8A is a diagram that illustrates an implant portion 90 coupled to a coupling mechanism 866 of a needle 860 when a sliding mechanism 840 is in a deployed configuration so that the needle 860 is moved outside of a guide 830 (e.g., a lumen portion 834 of the guide 830) of the internal arm 820 of a medical device 800. FIG. 8B is a diagram that illustrates the sliding mechanism 840 after being moved to a stowed configuration so that the needle 860, and the implant portion 90 coupled thereto, are moved inside of the guide 830 (e.g., the lumen portion 834 of the guide 830) of the internal arm 820. The implant portion 90 has at least a portion moved into a slot 874 of the internal arm 820.

Referring back to FIG. 7, at least a portion of the internal arm is inserted into a body of a patient such that an external arm coupled to the internal arm is disposed outside of the body of the patient (block 710). In some embodiments, all, or nearly all, of the external arm, including a receiving mechanism, may be disposed outside of a skin tissue of the patient. In some embodiments, the internal arm can be inserted into a vaginal region of a body of a patient or a rectal region of a body of a patient. In some embodiments, the internal arm can be inserted into the body of the patient after the portion of the implant is coupled to the coupling mechanism of the needle and after the needle has been retracted into the internal arm (e.g., into a guide of the internal arm).

Figure 8C:
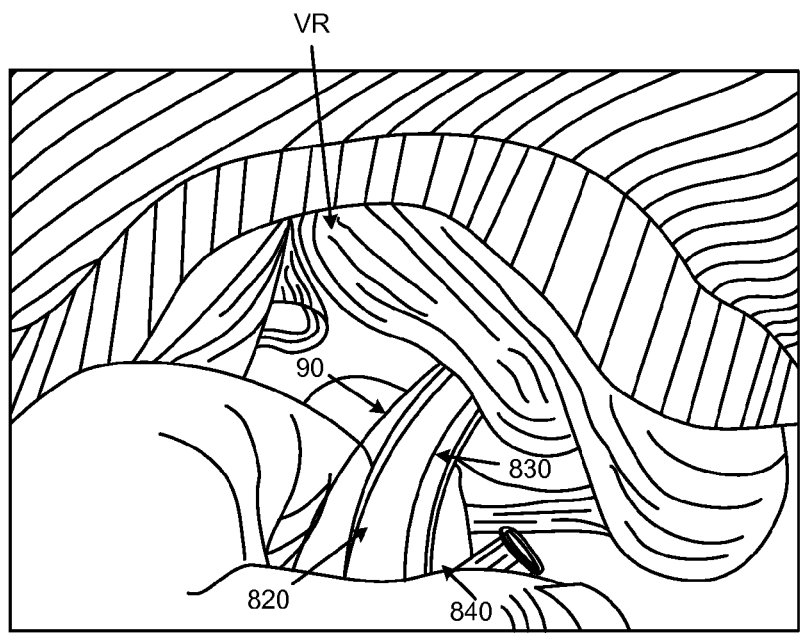
Figure 8D:
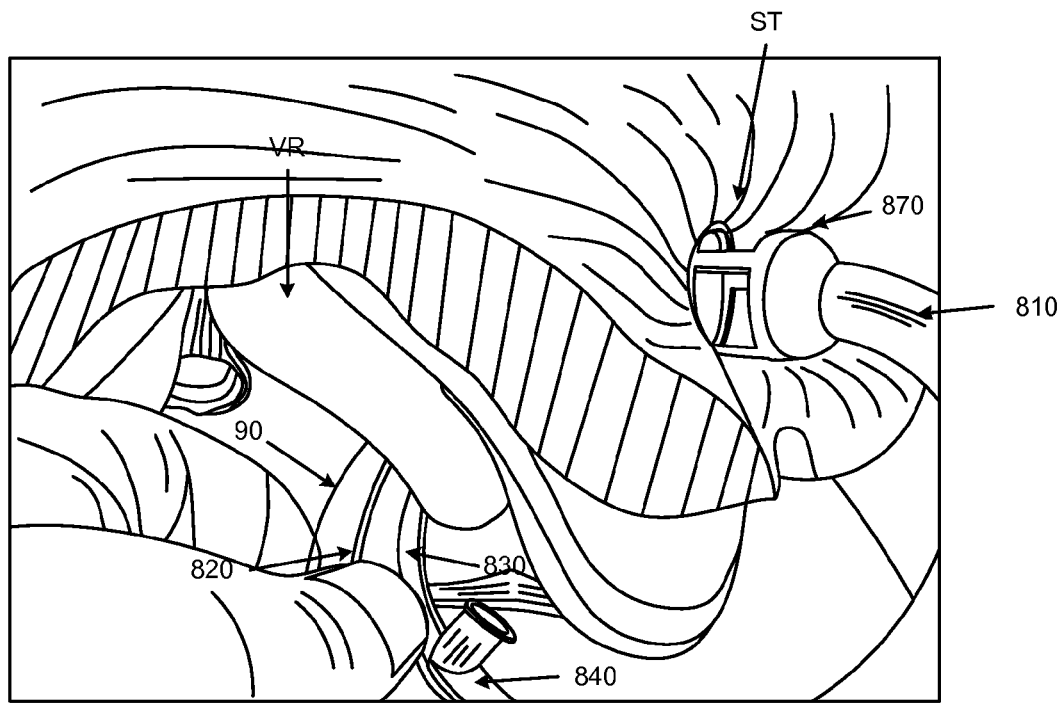

FIG. 8C is a diagram that schematically illustrates at least a portion of the internal arm 820 inserted into a body of a patient. Specifically, the internal arm 820 is inserted into a vaginal region VR of the body of the patient (for example, through a vaginal incision). In this embodiment, the internal arm 820 is inserted into the body of the patient after the implant portion 90 is coupled to the coupling mechanism of the needle 860 (not shown in FIG. 8C) and after the needle 860 has been retracted into the internal arm 820 (e.g., into a guide of the internal arm). In this embodiment, the sliding mechanism 840, and needle 860, are in a stowed configuration. As shown in FIG. 8D, the internal arm 820 is moved into the body of the patient such that the external arm 810 coupled to the internal arm 820 is disposed outside of the body of the patient.

Referring back to FIG. 7, the external arm coupled to the internal arm is moved toward the internal arm (block 720). The external arm can be moved from a first position to a second position toward the internal arm. In some embodiments, the internal arm can be rotatably coupled (e.g., hingedly coupled) to the external arm of the medical device. The external arm can be moved towards the internal arm until a receiving mechanism of the external arm is compressed against a skin tissue of the patient. In some embodiments, the external arm can be releasably locked in a position with respect to the internal arm. In some embodiments, a locking mechanism can be released (can be moved to an unlocked configuration) before the external arm is moved towards the internal arm.

FIG. 8D is a diagram that illustrates the external arm 810 after the external arm 810 is moved toward the internal arm 820. In the embodiment shown in FIG. 8D, the internal arm 820 is rotatably coupled (e.g., hingedly coupled) to the external arm 810. The external arm 810 is moved towards the internal arm 820 until a receiving mechanism 870 of the external arm 810 is compressed against a skin tissue ST of the patient.

Referring back to FIG. 7, a sliding component coupled to the internal arm is moved in a first direction along a guide of the internal arm toward the external arm such that the distal portion of a needle of the sliding component is moved out of the body of the patient (block 730). The sliding component can be moved in the first direction to a deployed configuration (from a stowed configuration) (or from a first position to a second position along a guide). The distal portion of the needle may have a distal tip that pierces a skin tissue of the body of the patient so that the distal portion of the needle may move out of the body of the patient. In some embodiments, the sliding component can be moved so that the distal portion of the needle, and the portion of the implant coupled thereto, can be moved out of the body of the patient. The portion of the implant may then be decoupled by a physician (e.g., by a physician using the hemostat) from the distal portion of the needle. In some embodiments, the distal portion of the needle may be moved out of the body of the patient and into a portion of the receiving mechanism, or at a location near the receiving mechanism. In such embodiments, the receiving mechanism can be used as an indicator of an approximate location that the distal portion of the needle may pierce through and exit a skin tissue of the body of the patient.

In some embodiments, the sliding component can be moved after a locking mechanism has been released (is moved to an unlocked configuration). In some embodiments, the sliding component can be biased away from the external arm so that a force must be applied to the sliding component to move the sliding component towards the external arm. In some embodiments, the sliding component can be biased toward the external arm so that the sliding component (and needle) moves toward the external arm in response to a locking mechanism being released.

Although not shown in the flow diagram, in some embodiments, the internal arm of the medical device may be configured so that a coupling mechanism of the needle may be coupled to at least a portion of an implant as the sliding mechanism is moved to a deployed configuration. In such embodiments, the portion of the implant may be coupled to a slot included in the internal arm so that as the sliding mechanism is moved to the deployed configuration and the needle is moved out of a guide of the internal arm, the coupling mechanism of the needle may be coupled to the portion of the implant. As the sliding mechanism continues to move to the deployed configuration, the needle, and the portion of the implant coupled thereto, may be moved out of the body of the patient so that the portion of the implant may be retrieved by a physician.

Figure 8E:
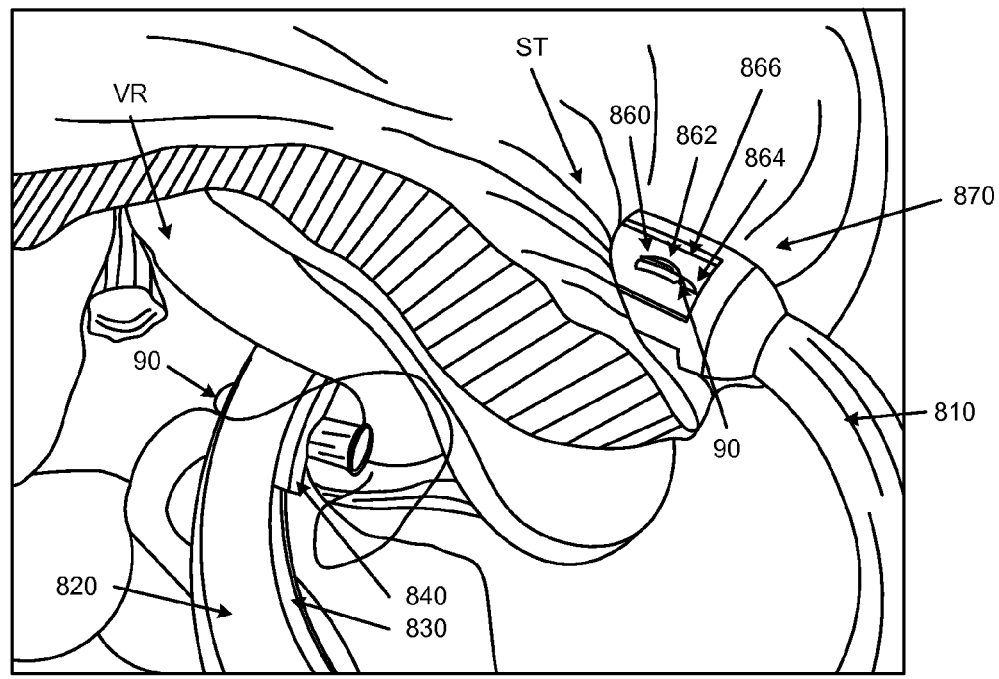
Figure 8F:
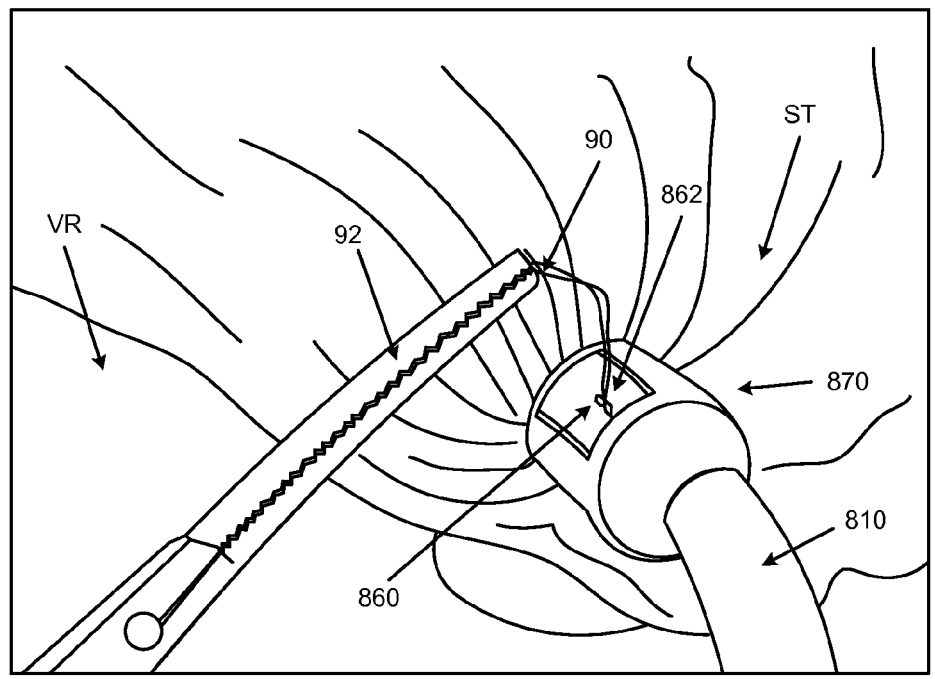

FIG. 8E illustrates the sliding component 840 coupled to the internal arm 820 moved in a first direction along the guide 830 of the internal arm 820 toward the external arm 810 such that the distal portion of the needle 860 of the sliding component 840 is moved out of the body of the patient. The sliding component 840 can be moved in the first direction to a deployed configuration (from a stowed configuration) (or from a first position to a second position along the guide 830). The distal portion 862 of the needle 860 has a distal tip 864 that has pierced the skin tissue ST of the body of the patient so that the distal portion 862 of the needle 860 is moved out of the body of the patient. As shown in FIG. 8D, the sliding component 840 is moved so that the distal portion 862 of the needle 860, and the implant portion 90 coupled thereto, are moved out of the body of the patient. As shown in FIG. 8F, the implant portion 90 may be decoupled by a physician (e.g., by a physician using a hemostat 92) from the distal portion 862 of the needle 860. In this embodiment, the distal portion 862 of the needle 860 is moved out of the body of the patient and into a portion of the receiving mechanism 870 of the external arm 810.

Referring back to FIG. 7, the sliding component coupled to the internal arm is moved in a second direction along the guide of the internal arm away from the external arm until the distal portion of the needle is retracted into the internal arm (block 740). Moving the sliding component in the second direction can change the sliding component from the deployed configuration to a stowed configuration. In some embodiments, the distal portion of the needle may be retracted into a guide of the internal arm, or a lumen of the guide of the internal arm. In some embodiments, the internal arm can be biased (e.g., biased with a spring mechanism) away from the external arm so that the internal arm automatically moves away from the external arm.

Figure 8G:
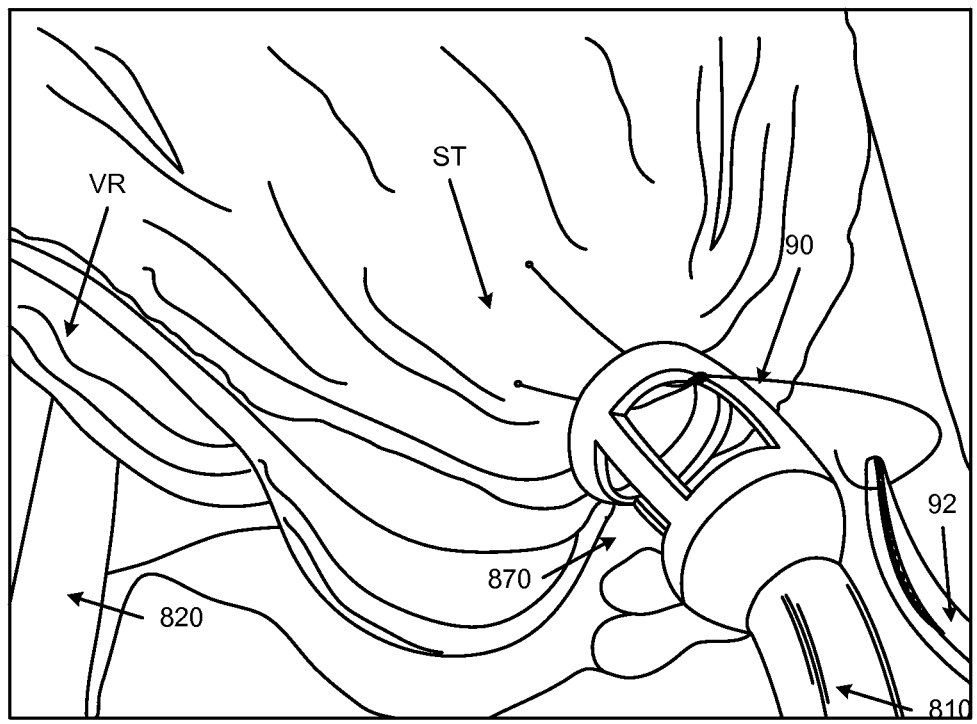

FIG. 8G is a diagram that illustrates the external arm 810 moved away from the internal arm 820 after the needle 860 (not shown in FIG. 8G) has been retracted into the internal arm 820. In some embodiments, the sliding component 840 (not shown in FIG. 8G) can be moved from the deployed configuration to the stowed configuration so that the needle 860 is retracted.

In a general aspect, a medical device can include an external arm having a receiving mechanism, and an internal arm coupled to the external arm such that the receiving mechanism of the external arm is movable with respect to the internal arm. The medical device can also include a sliding component including a needle configured to be coupled to a portion of an implant and configured to slidably move the needle toward the receiving mechanism of the external arm.

In some embodiments, the internal arm has a guide configured to rotatably move about an axis toward the external arm from a first position with respect to the external arm to a second position with respect to the external arm. The sliding component can be configured to slidably move along the guide when the guide is in the first position with respect to the external arm and configured to slidably move along the guide when the guide is in the second position with respect to the external arm. In some embodiments, the internal arm has a guide, and the needle is configured to slidably move within the guide and configured to move into at least a receiving mechanism of the external arm.

In some embodiments, the internal arm is configured to be inserted into a body of a patient after the needle is coupled to the portion of the implant. The sliding component can be configured to slidably move the portion of the implant within a guide included in the internal arm toward the receiving mechanism of the external arm after the receiving mechanism of the external arm is moved toward the portion of the guide. In some embodiments, the internal arm is configured to be inserted into a body of a patient after the needle is coupled to the portion of the implant, and the receiving mechanism of the external arm is configured to be disposed outside of the body of the patient when the internal arm is inserted into the body of the patient.

In some embodiments, the guide of the internal arm defines a lumen. The needle is configured to slidably move within the lumen when the sliding component is slidably moved along the guide of the internal arm. In some embodiments, the internal arm has a guide, and the guide has an inner surface of a concave portion facing toward the receiving mechanism of the external arm. In some embodiments, the needle of the sliding component defines a lumen therethrough, the sliding component defines an opening being in fluid communication with the lumen defined by the needle and configured to receive a fluid to be conveyed through the lumen.

In some embodiments, the needle has a coupling mechanism configured to be releasably coupled to the portion of the implant. In some embodiments, the external arm has an indicator configured to represent a distance between the portion of the guide of the internal arm and the receiving mechanism of the external arm.

In another general aspect, a medical device can include an internal arm defining a guide, and an external arm coupled to the internal arm and having a receiving mechanism configured to move from a first position to a second position such that a distance between the guide of the internal arm and the receiving mechanism of the external arm is decreased. The medical device can also include a sliding component including a needle and configured to slidably move along the guide such that a distal portion of the needle is moved toward the receiving mechanism of the external arm.

In some embodiments, the distal portion of the needle is configured to be coupled to a portion of an implant, and the internal arm is configured to be inserted into a body of a patient after the needle is coupled to the portion of the implant. The receiving mechanism of the external arm can be configured to be disposed outside of the body of the patient when the internal arm is inserted into the body of the patient.

In some embodiments, the distal portion of the needle is configured to be coupled to a portion of an implant, and the sliding component is configured to slidably move the needle within the guide of the internal arm until the portion of the implant coupled to the portion of the needle is moved through a skin tissue of a patient and is disposed on a same side of the skin tissue as the receiving mechanism of the external arm. In some embodiments, the sliding component is configured to slidably move after the distance between the guide and the external arm has been decreased.

In some embodiments, the medical device can include a locking mechanism configured to removably lock the internal arm in a position with respect to the external arm when the distance between the guide and the external arm is decreased. In some embodiments, the guide is a first guide, and at least one of the internal arm and the external arm is configured to slidably move along a second guide such that the distance between the first guide and the external arm is decreased. In some embodiments, the internal arm is configured to be inserted into a vaginal region of a patient, the needle is configured to pierce a skin tissue of the patient when the needle is moved toward the receiving mechanism of the external arm.

In yet another general aspect, a method can include inserting at least a portion of an internal arm including a needle coupled to at least a portion of an implant into a body of a patient such that an external arm coupled to the internal arm is disposed outside of the body of the patient. The method can also include moving a component such that the portion of the implant coupled to the needle of the sliding component is moved along a guide of the internal arm toward the external arm and outside of the body of the patient.

In some embodiments, the method can include decoupling the portion of the implant from the needle after the portion of the implant is disposed outside of the body of the patient, and adjusting a position of a sling of the implant within the body of the patient using the portion of the implant after the decoupling. In some embodiments, the method can include moving, before the moving of the sliding component, the external arm toward the internal arm.

In some embodiments, the method can include decoupling the portion of the implant from the needle after the portion of the implant is disposed outside of the body of the patient. In some embodiments, the moving can include moving the sliding component in a first direction. The method can include decoupling the portion of the implant from the needle after the portion of the implant is disposed outside of the body of the patient, and moving, after the decoupling, the sliding component coupled in a second direction until the needle is disposed inside of the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   an internal arm defining a guide disposed along at least a portion of a length of the internal arm;
   an external arm pivotally coupled to the internal arm, the external arm having a receiving mechanism, the external arm configured to move from a first position to a second position such that a distance between the guide of the internal arm and the receiving mechanism of the external arm is decreased;
   a needle slidably coupled to the internal arm such that at least a portion of the needle slides along the guide, the needle including a distal end portion configured to be coupled to a portion of an implant, the needle defining a lumen;
   a sliding component coupled to the needle, the sliding component configured to slide along the guide and move the needle toward the receiving mechanism of the external arm, wherein movement of the sliding component in a direction towards the receiving mechanism is limited when the sliding component reaches an end of the guide; and
   a syringe configured to be coupled to the sliding component, the syringe configured to be fluidly coupled to a proximal end portion of the needle, the syringe configured to deliver or draw fluid via the lumen of the needle.

2. The medical device of claim 1, wherein the distal end portion of the needle is configured to be coupled to the portion of the implant, the internal arm is configured to be inserted into a body of a patient after the needle is coupled to the portion of the implant, the receiving mechanism of the external arm is configured to be disposed outside of the body of the patient when the internal arm is inserted into the body of the patient.

3. The medical device of claim 1, wherein the distal end portion of the needle is configured to the coupled to the portion of the implant, the sliding component is configured to slidably move the needle along the guide of the internal arm until the portion of the implant coupled to the portion of the needle is moved through a skin tissue of a patient and is disposed on a same side of the skin tissue as the receiving, mechanism of the external arm.

4. The medical device of claim 1, wherein the sliding component is configured to slidably move after the distance between the guide and the external arm has been decreased.

5. The medical device of claim 1, further comprising:
   a locking mechanism configured to removably lock the internal arm in a position with respect to the external arm when the distance between the guide and the external arm is decreased.

6. The medical device of claim 1, wherein the internal arm includes a distal portion defining at least one slot configured to receive the implant.

7. The medical device of claim 1, wherein the internal arm has a curved shape defining a first radius of curvature, and the external arm has a curved shape defining a second radius of curvature, the second radius of curvature being substantially the same as the first radius of curvature.

8. A method, comprising:
   inserting at least a portion of an internal arm into a body of a patient such that an external arm pivotally coupled to the internal arm is disposed outside of the body of the patient, at least a portion of a needle being disposed within the internal arm and moveable along a groove of the internal arm, the needle coupled to a portion of an implant, the internal arm including a sliding component coupled to the needle; and
   moving the sliding component of the internal arm such that the portion of the implant coupled to the needle is moved along the groove of the internal arm toward a receiving mechanism of the external arm and outside of the body of the patient, the receiving mechanism defining a cavity on the external arm, wherein movement of the sliding component in a direction towards the receiving mechanism is limited when the sliding component reaches an end of the groove.

9. The method of claim 8, further comprising:
   decoupling the portion of the implant from the needle after the portion of the implant is disposed outside of the body of the patient; and
   adjusting a position of a sling of the implant within the body of the patient using the portion of the implant after the decoupling.

10. The method of claim 8, further comprising:
    moving, before the moving of the sliding component, the external arm toward the internal arm.

* * * * *